US012336724B2

(12) United States Patent
Alspaugh et al.

(10) Patent No.: US 12,336,724 B2
(45) Date of Patent: Jun. 24, 2025

(54) MINIMALLY INVASIVE TOOLS, SYSTEMS AND METHODS

(71) Applicant: WRIGHT MEDICAL TECHNOLOGY, INC., Memphis, TN (US)

(72) Inventors: Julia C. Alspaugh, Memphis, TN (US); Daniel E. Free, Oakland, TN (US); Braham K. Dhillon, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 345 days.

(21) Appl. No.: 17/760,487

(22) PCT Filed: Mar. 8, 2021

(86) PCT No.: PCT/US2021/021335
§ 371 (c)(1),
(2) Date: Aug. 10, 2022

(87) PCT Pub. No.: WO2021/206835
PCT Pub. Date: Oct. 14, 2021

(65) Prior Publication Data
US 2023/0136212 A1 May 4, 2023

Related U.S. Application Data

(60) Provisional application No. 63/008,034, filed on Apr. 10, 2020.

(51) Int. Cl.
A61B 17/17 (2006.01)
A61B 90/00 (2016.01)

(52) U.S. Cl.
CPC .. *A61B 17/1775* (2016.11); *A61B 2090/3966* (2016.02)

(58) Field of Classification Search
CPC . A61B 17/17; A61B 17/1739; A61B 17/1775; A61B 17/171; A61B 17/16;
(Continued)

(56) References Cited

U.S. PATENT DOCUMENTS 5,630,814 A * 5/1997 Ross, Jr. ............... A61B 17/62
606/56
2006/0229730 A1 10/2006 Railey et al.
(Continued)

FOREIGN PATENT DOCUMENTS

EP 2997926 B1 9/2019
WO 2008139167 A2 11/2008

OTHER PUBLICATIONS

International Search Report and Written Opinion issued in connection with International Patent Application No. PCT/US2021/021335, Jul. 23, 2021, 21 pages.

*Primary Examiner* — Christopher J Beccia
(74) *Attorney, Agent, or Firm* — DUANE MORRIS LLP

(57) ABSTRACT

A system includes a first tool having a base, a nut, and a tool guide. The base extends from a first end to a second end and includes at least one thread disposed along a length thereof. The first end includes a foot having a widthwise dimension that is greater than a diameter of the at least one thread. The nut is configured to be disposed along the length of the base and to engage at least one thread. The tool guide is configured to be slideably disposed along the length of the base and has a body including a flange portion. The flange portion defines an opening for receiving at least one of a pin and a cutting tool. Rotation of the first nut causes the nut to
(Continued)

translate along the length of the base thereby causing the tool guide to move along the length of the base.

6 Claims, 22 Drawing Sheets

(58) Field of Classification Search
CPC . A61B 17/1642; A61B 17/1682; A61B 17/15; A61B 17/157; A61B 17/64; A61G 13/12; A61G 13/125
See application file for complete search history.

(56) References Cited

U.S. PATENT DOCUMENTS

2006/0235420 A1\* 10/2006 Irving ................ A61B 17/1764
  606/87
2019/0029700 A1\* 1/2019 Free ................... A61B 17/1682

\* cited by examiner

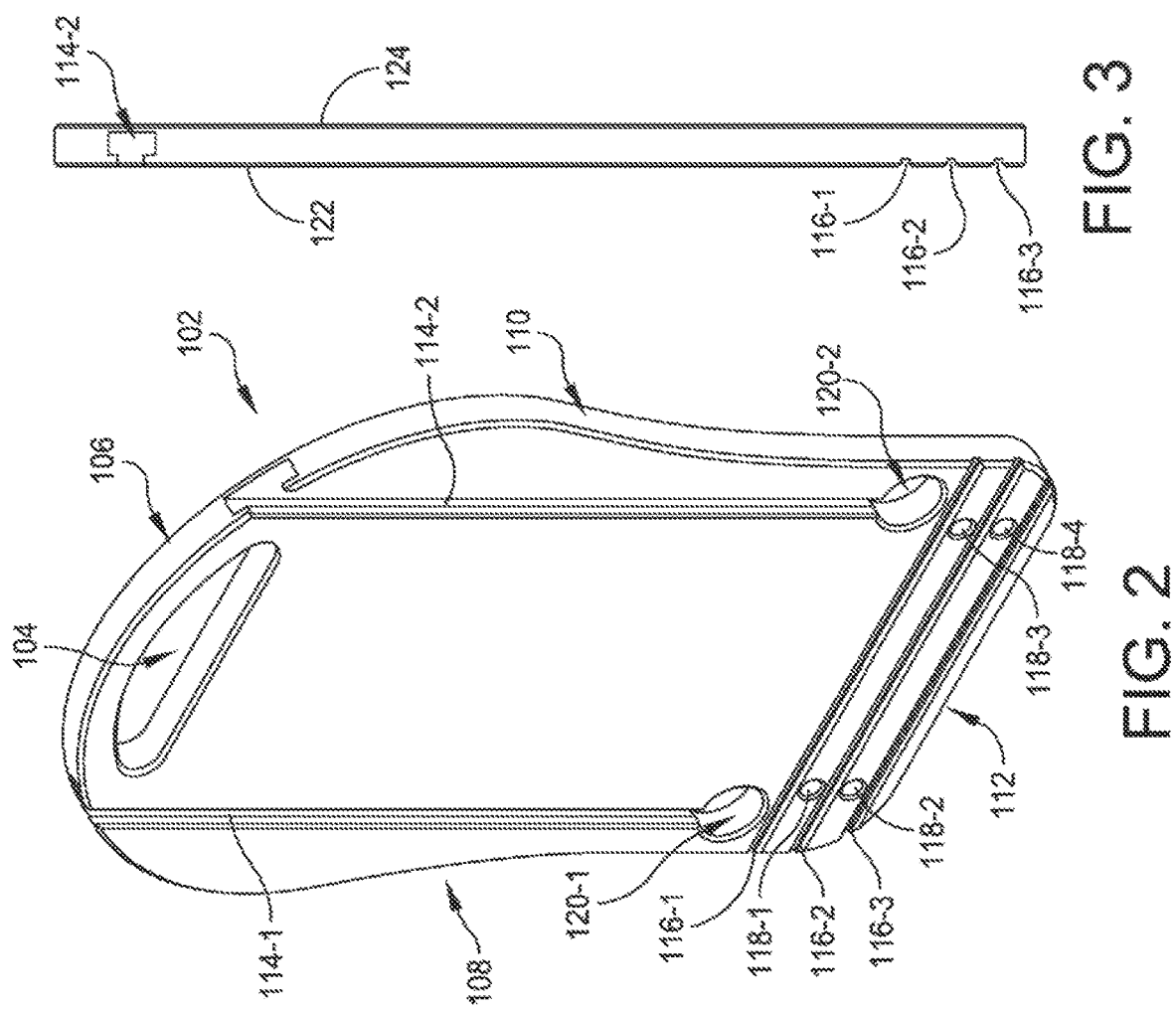

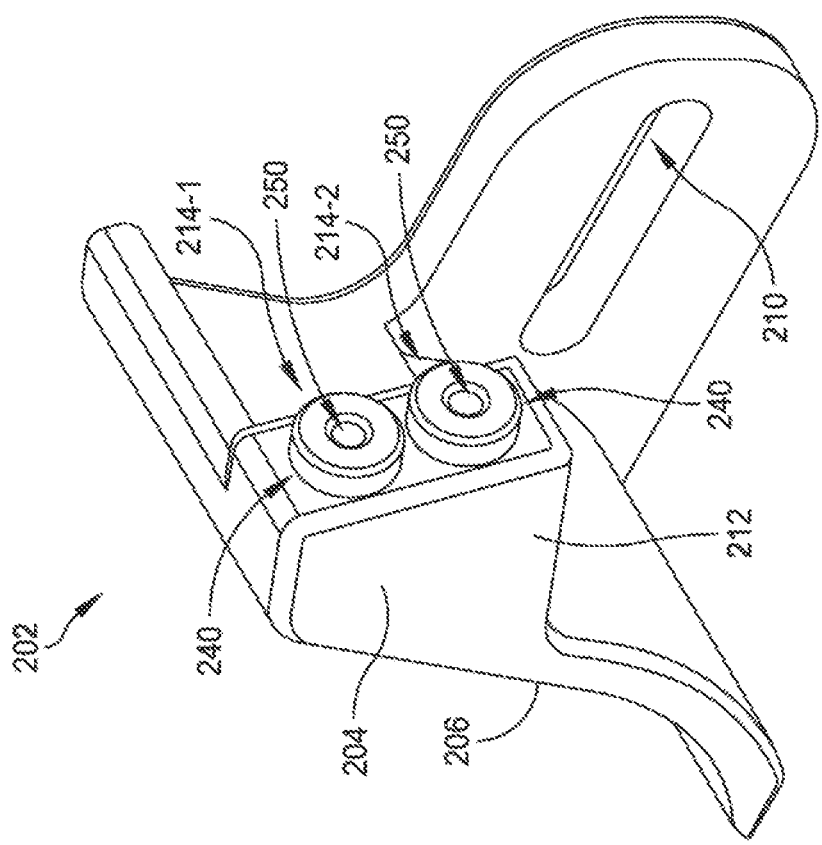

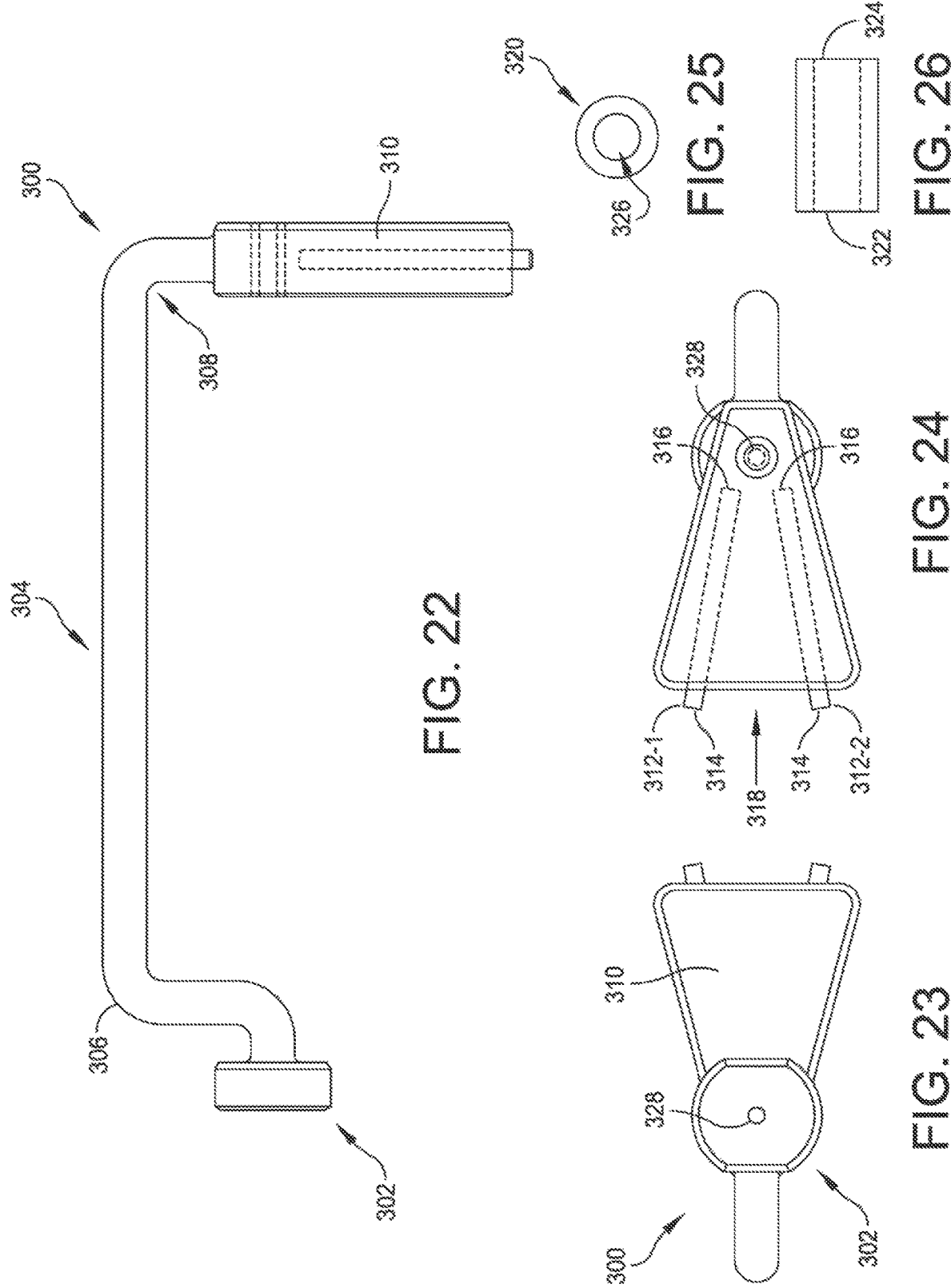

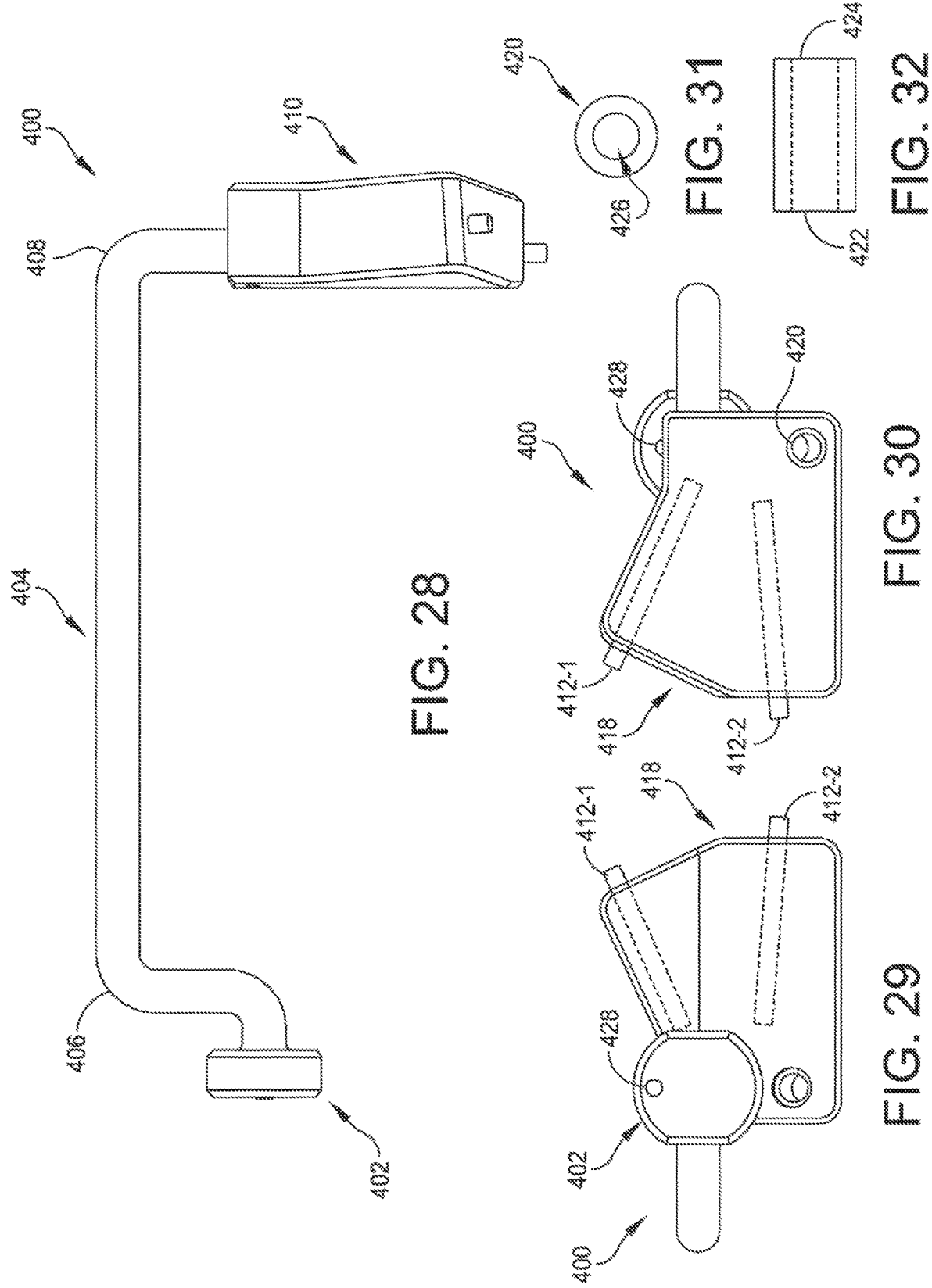

MINIMALLY INVASIVE TOOLS, SYSTEMS AND METHODS

CROSS-REFERENCE TO RELATED APPLICATIONS

This application is a National Stage Application, filed under 35 U.S.C. 371, of International Patent Application No. PCT/US2021/021335, filed on Mar. 8, 2021, which claims priority to U.S. Provisional Application No. 63/008,034, filed on Apr. 10, 2020, the entire contents are incorporated herein by reference.

FIELD OF DISCLOSURE

The disclosed systems are directed to fixtures and guides for use in surgeries. More particularly, the disclosed systems are directed to fixtures and guides for use in minimally invasive surgical (MIS) procedures, including MIS for Charcot neuropathy procedures involving extremities such as the hand and foot.

BACKGROUND

Many minimally invasive surgeries (MIS) or surgical procedures, such as those involving bunions, osteotomies, and fusions, involve making cuts with burrs. Physicians or surgeons typically make these cuts without any guidance. As such, these procedures and the making of these cuts are typically considered to be an "art" as opposed to a science. Thus, the outcome of the surgery is largely dependent on the skill level of the surgeon and the ability to perform the surgery with consistency is difficult if not impossible. The disclosed systems are especially useful in planning for complex limb salvage procedures, such as fractures, non-unions, or deformities including Charcot neuropathy, which demand a high level of accuracy with reduced incisions.

SUMMARY

In some embodiments, a system includes a first tool having a base, a nut, and a tool guide. The base extends from a first end to a second end and includes at least one thread disposed along a length thereof. The first end includes a foot having a widthwise dimension that is greater than a diameter of the at least one thread. The nut is configured to be disposed along the length of the base and to engage at least one thread. The tool guide is configured to be slideably disposed along the length of the base and has a body including a flange portion. The flange portion defines an opening for receiving at least one of a pin and a cutting tool. Rotation of the first nut causes the nut to translate along the length of the base thereby causing the tool guide to move along the length of the base.

In some embodiments, a system includes a base plate formed from a radiolucent material. The base plate includes a first side and a second side. The first side of the base plate defines at least one first channel and at least one second channel. The at least one first channel extends along a length of the base plate in a first direction. The at least one second channel extends along a width of the based plate in a second direction, which is different from the first direction. The base plate further defines at least one first hole extending inwardly from the first side and at least partially overlapping the at least one first channel such that the hole is in communication with the at least one first channel.

A method includes securing a body part to a base plate formed from a radiolucent material; coupling at least one first tool to the base plate, the at least one tool configured for providing fluoroscopic guidance without physically contacting the body part; and performing a minimally invasive surgical procedure on the body part using the at least one first tool.

A system includes a base plate formed from a radiolucent material and a first tool. The base plate includes a first side and a second side. The first side of the base plate defines a first channel and a second channel that extend along a length of the base plate in a first direction. The first tool includes a first component including a first foot and a first body and a second component including a second foot and a second body. The first foot is sized and configured to be received in at least one of the first channel and the second channel defined by the base plate. The first body supports at least one first radiopaque member. The second foot is sized and configured to be received in at least one of the first channel and the second channel defined by the base plate. The second body supports at least one second radiopaque member. The at least one first radiopaque member of the first component and the at least one second radiopaque member are configured to provide a visual indication of proper alignment of the first component, second component, and a fluoroscope when the first component is disposed within one of the first and second channels and the second component is disposed within another of the first and second channels.

BRIEF DESCRIPTION OF THE DRAWINGS

FIG. 2 is an isometric view of one example of a base plate in accordance with some embodiments;

FIG. 3 is a lateral side view of the base plate illustrated in FIG. 2 in accordance with some embodiments;

FIG. 4 is an end side view of the base plate illustrated in FIG. 2 in accordance with some embodiments;

FIG. 8 is an isometric view of a component of the foot clamp illustrated in FIG. 7 in accordance with some embodiments;

FIG. 22 is a side view of the guidance tool illustrated in FIG. 21 in accordance with some embodiments;

FIG. 23 is a bottom side view of the guidance tool illustrated in FIG. 21 in accordance with some embodiments;

FIG. 24 is a top side view of the guidance tool illustrated in FIG. 21 in accordance with some embodiments;

FIG. 25 is an end view of one example of a radiopaque element that may be used with the guidance tool illustrated in FIG. 21 in accordance with some embodiments;

FIG. 26 is a side view of the radiopaque element illustrated in FIG. 25 in accordance with some embodiments;

FIG. 28 is a side view of the guide tool illustrated in FIG. 27 in accordance with some embodiments;

FIG. 29 is a bottom side view of the guide tool illustrated in FIG. 27 in accordance with some embodiments;

FIG. 30 is a top side view of the guide tool illustrated in FIG. 27 in accordance with some embodiments;

FIG. 31 is an end view of one example of a radiopaque member that may be used in connection with the guide tool illustrated in FIG. 27 in accordance with some embodiments;

FIG. 32 is a side view of the radiopaque member illustrated in FIG. 31 in accordance with some embodiments;

DETAILED DESCRIPTION

This description of the exemplary embodiments is intended to be read in connection with the accompanying drawings, which are to be considered part of the entire written description.

The disclosed systems, guides, fixtures, and tools advantageously enable improved surgical outcomes by providing a surgeon or other medical professional with fluoroscopic and/or actual physical guidance when performing MIS procedures. For example, the disclosed systems, guides, fixtures, and tools enable a surgeon to secure an extremity, such as a hand or foot, to a base plate and perform MIS procedures (e.g., Charcot neuropathy procedures) with the aid of fluoroscopy. Further, the disclosed tools and systems may be provided in a variety of sizes and/or shapes for performing various surgical techniques or cuts. For example, a guide or pair of guides may be provided in one or more sizes and provide guidance for providing one or more cuts at one or more angles. Advantageously, the disclosed tools and systems may provide guidance without the need for actually contacting the patient as described below. The selection of the one or more tools or systems (e.g., size and/or shape) may be made by a surgeon preoperatively (i.e., based on preoperative planning or imaging) or intraoperatively. The ability to guide cutting or drilling tools that limit the amount of patient contact contribute to a less invasive surgical procedure and faster recovery times.

Figure 1:
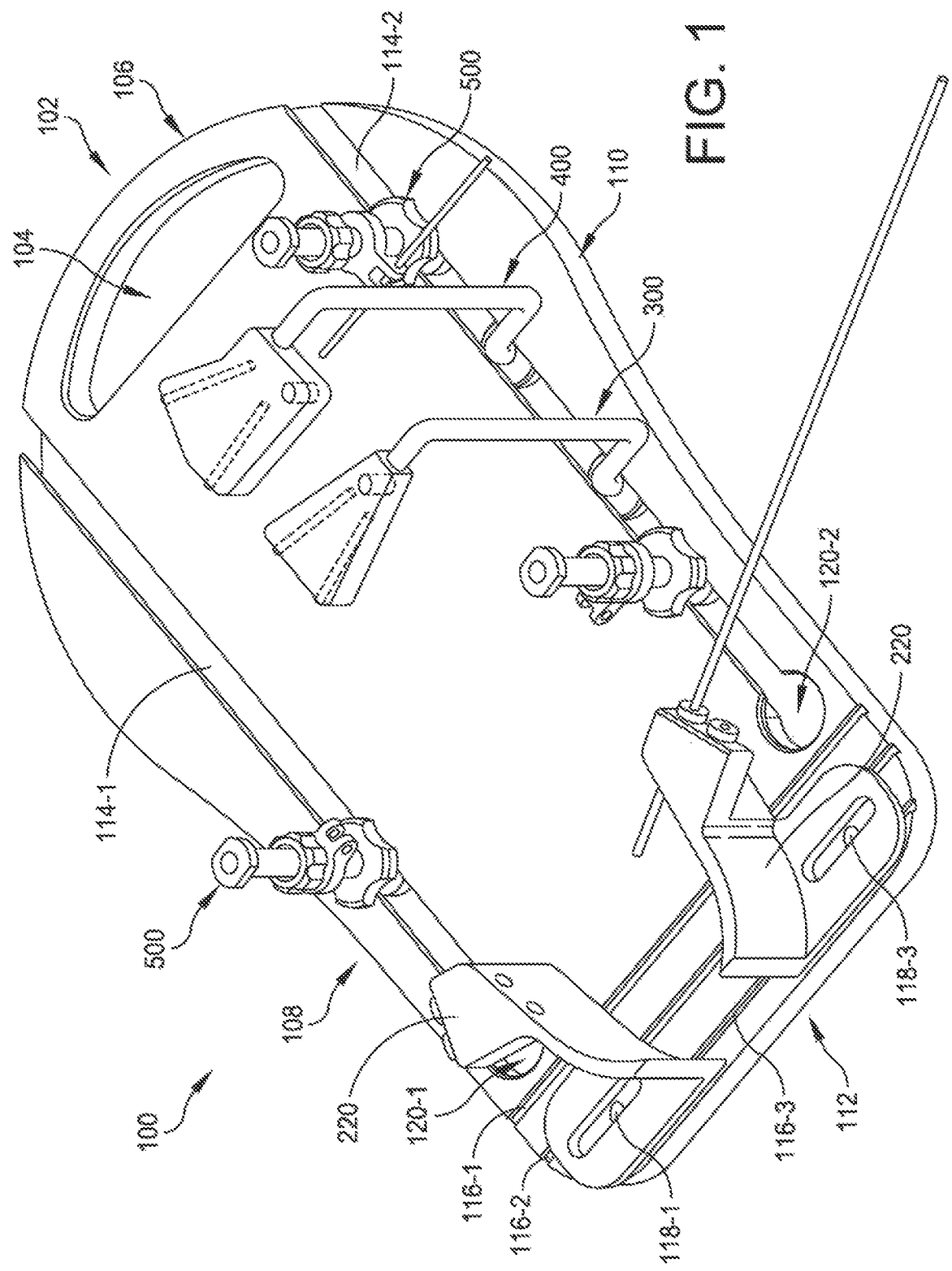
FIG. 1 is an isometric view of one example of a fixture in accordance with some embodiments.

FIG. 1 illustrates one example of a system or fixture for use in performing a MIS procedure. As shown in FIG. 1, the system or fixture includes a base plate 102 for supporting an extremity. Although base plate 102 is shown as being a foot plate, a person of ordinary skill in the art will understand that the disclosure is not so limited and that the base plate 102 could be used to support a hand, arm, wrist, or other extremity. In some embodiments, base plate 102 is formed from a rigid radiolucent material that may be sterilized. Examples of such materials include, but are not limited to, polyetheretherketone (PEEK), polyphenylsulfone (PPSU), polyacetal (POM-C), and polypropylene, to list only a few possibilities. Providing a radiolucent base plate 102 enables the extremity being supported by the base plate to be imaged using radiography from above (i.e., looking down onto the base plate). A person of ordinary skill in the art will appreciate that the base plate may also be formed from a radiopaque material in some embodiments.

Figure 6:
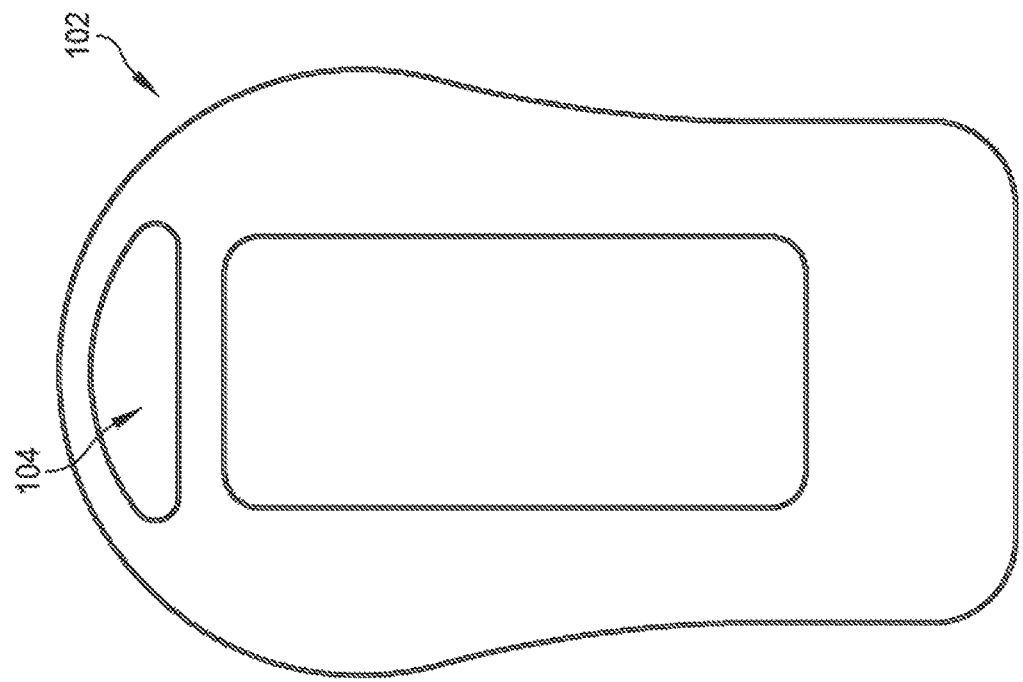
FIG. 6 is a bottom side plan view of the base plate illustrated in FIG. 2 in accordance with some embodiments.
Figure 5:
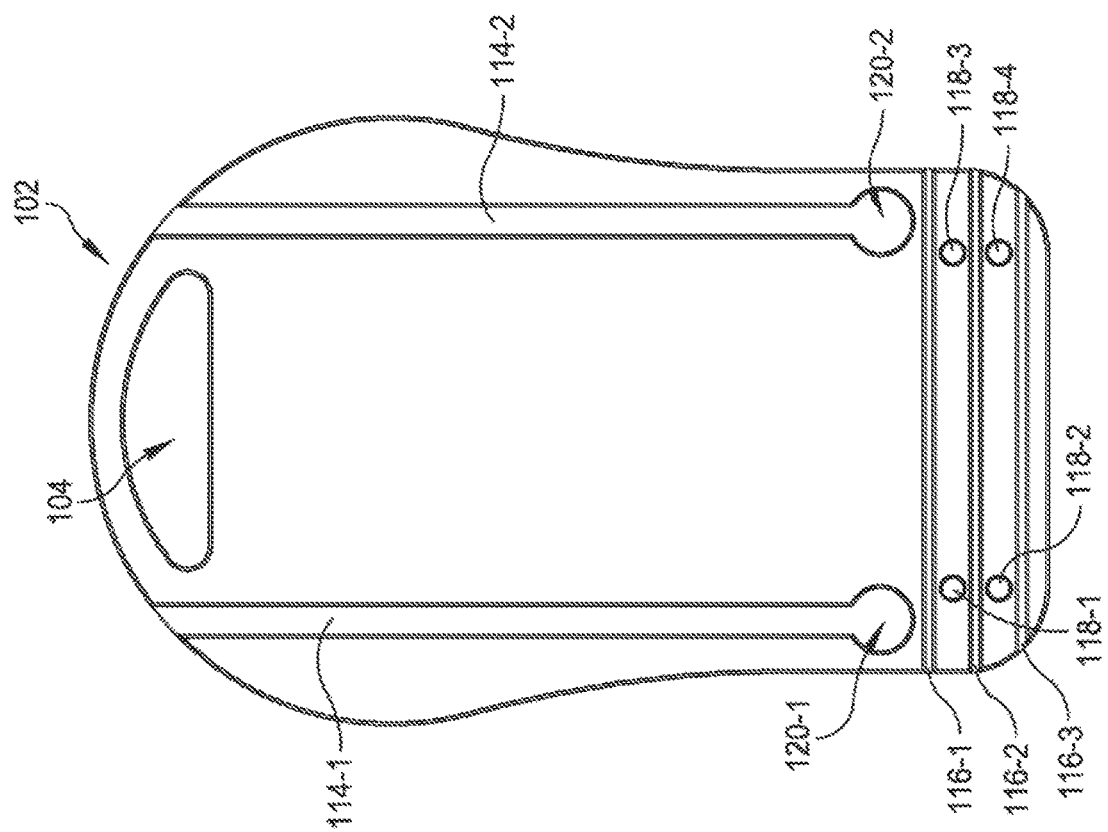
FIG. 5 is a top side plan view of the base plate illustrated in FIG. 2 in accordance with some embodiments.

Base plate 102 is shown in FIGS. 2-6 having a generally rectangular shape, although one of ordinary skill in the art will understand that base plate 102 may have other shapes. As best seen in FIGS. 2, 5, and 6, base plate 102 has a length that is greater than a width to accommodate a human foot, which typically is longer than it is wide. The thickness of base plate 102 may also vary, although the thickness of base plate 102 should have a sufficient thickness to be suitable rigid for supporting an extremity.

In some embodiments, base plate 102 defines at least one opening 104 (FIGS. 2, 5, and 6), which may serve as a handle for carrying the base plate 102. The opening 104 may be positioned adjacent to a first side 106 and have a length that extends in a widthwise direction across base plate 102. However, one of ordinary skill in the art will understand that opening 104 could be provided along one of the sides 108, 110 directly adjacent to side 106 or could be provided adjacent to side 112, which is located opposite side 106.

In some embodiments, base plate 102 also defines one or more first channels (e.g., channels 114-1, 114-2; collectively "channels 114") for use in securing tools (described in greater detail below) to base plate 102. As shown in FIG. 5, channels 114 extend from side 106 in a direction parallel to a longitudinal axis defined by base plate 102. Base plate 102 may also define one or more second channels (e.g., channels 116-1, 116-2, 116-3; collectively "channels 116"). Channels 116 may extend in a widthwise direction from side 108 to side 110 such that channels 116 extend perpendicular to channels 114. In some embodiments, the width of channels 114 and 116 is different; however, one of ordinary skill in the art will understand that the width of channels 114 and 116 may be the same.

Although channels 114 and 116 are shown as having a generally square cross-sectional geometry, one of ordinary skill in the art will understand that channels 114 and/or 116 may have other cross-sectional geometries. For example, channels 114 and/or 116 may include undercuts or dovetails to facilitate the securement of one or more tools to base plate 102.

In some embodiments, channels 114-1, 114-2 respectively terminate at an enlarged hole 120-1, 120-2 (collectively, "enlarged holes 120" or "holes 120"), which extends through base plate 102, i.e., from an upper side 122 to a lower side 124. As described in greater detail below, holes 120 facilitate the placement or removal of one or more tools without having the slide the tools out via the opening of the channels 114 located at the side 106 of base plate 102.

The number and type of tools that may be secured to base plate 102 may be of a variety of types and sizes depending on the type of MIS procedure. For example, the tools may include pin holders and fluoroscopic visualization tools, to list only a couple of examples.

Figure 7:
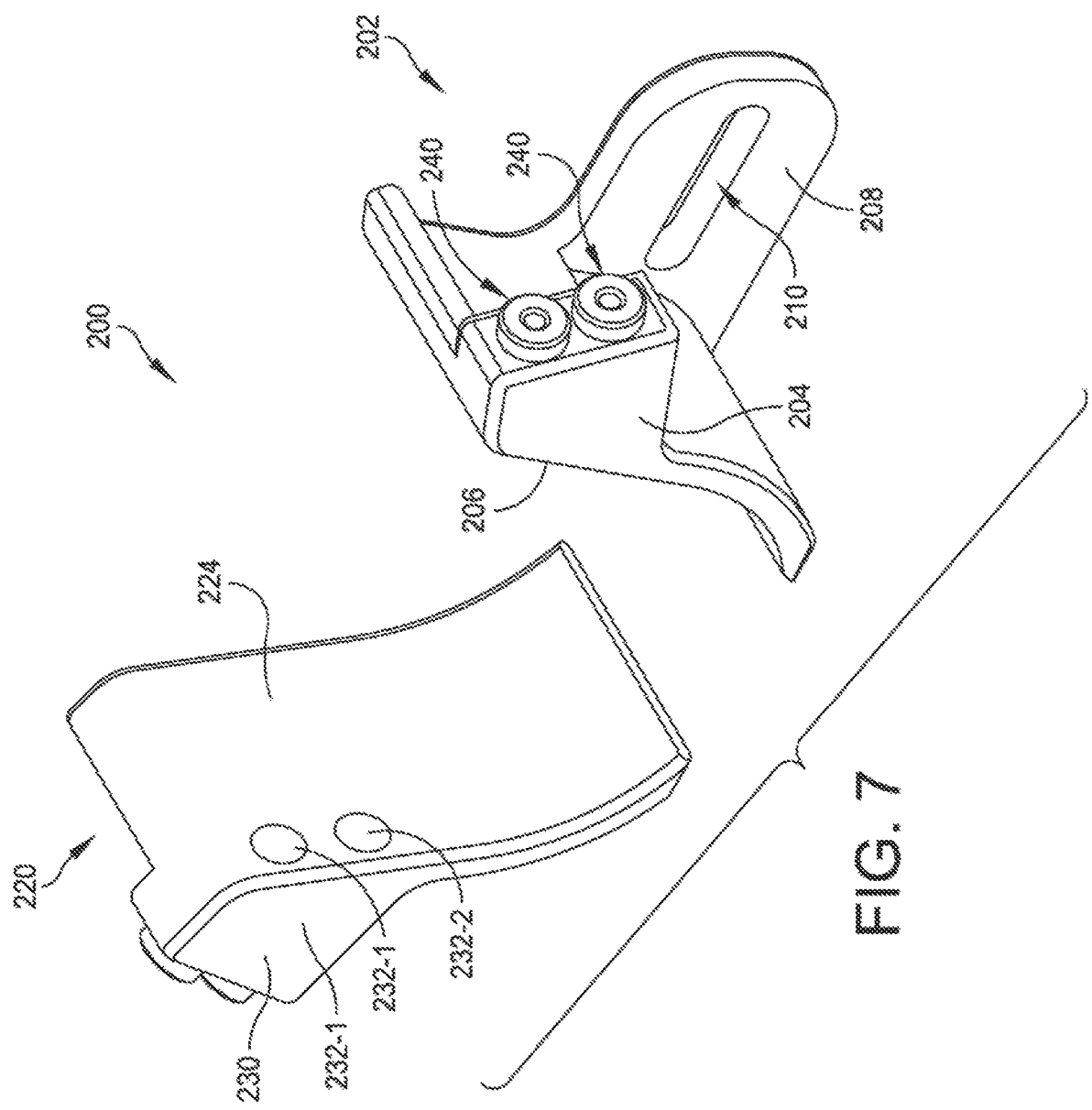
FIG. 7 is an isometric view of one example of a foot clamp in accordance with some embodiments.
Figure 10:
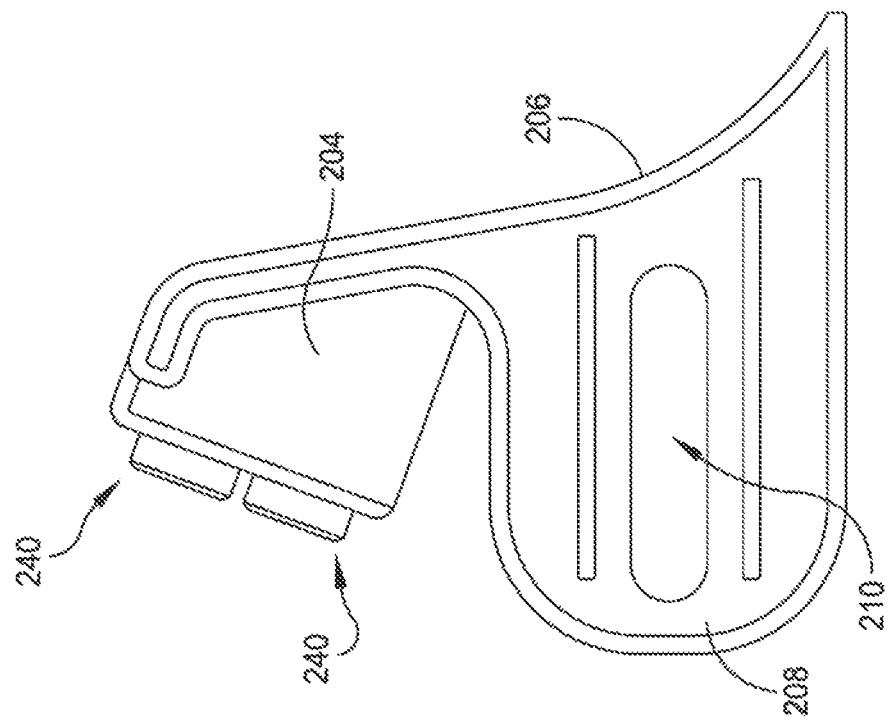
FIG. 10 is a bottom side plan view of the foot clamp component illustrated in FIG. 8 in accordance with some embodiments.
Figure 9:
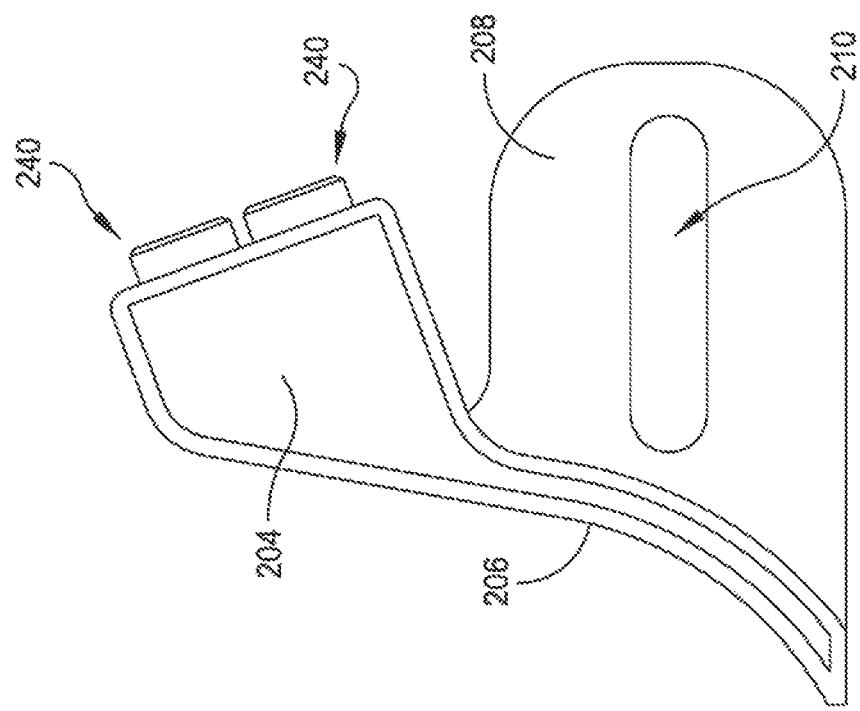
FIG. 9 is a top side plan view of the foot clamp component illustrated in FIG. 8 in accordance with some embodiments.
Figure 11:
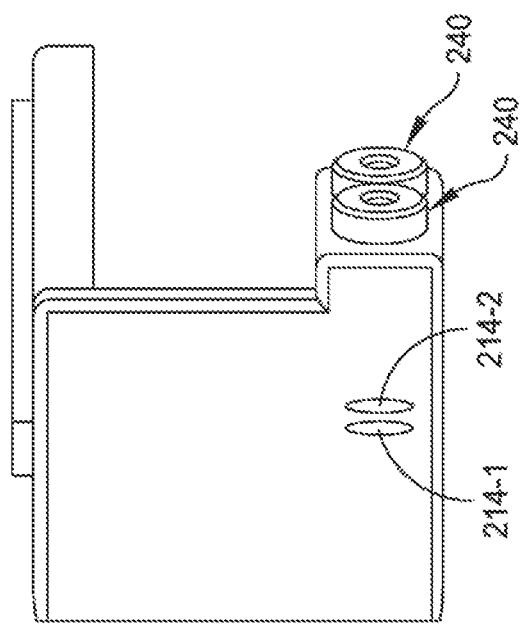
FIG. 11 is an end view of the foot clamp component illustrated in FIG. 8 in accordance with some embodiments.
Figure 12:
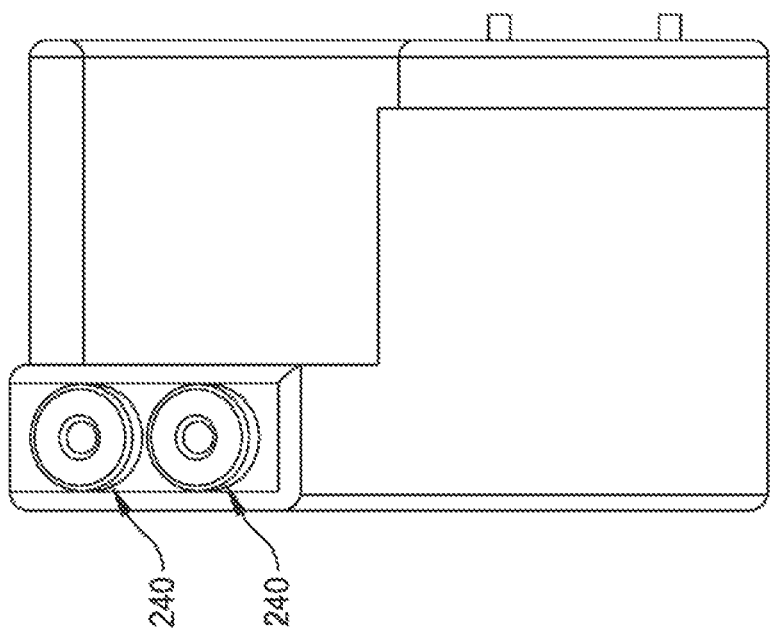
FIG. 12 is a side view of the foot clamp component illustrated in FIG. 8 in accordance with some embodiments.
Figure 13:
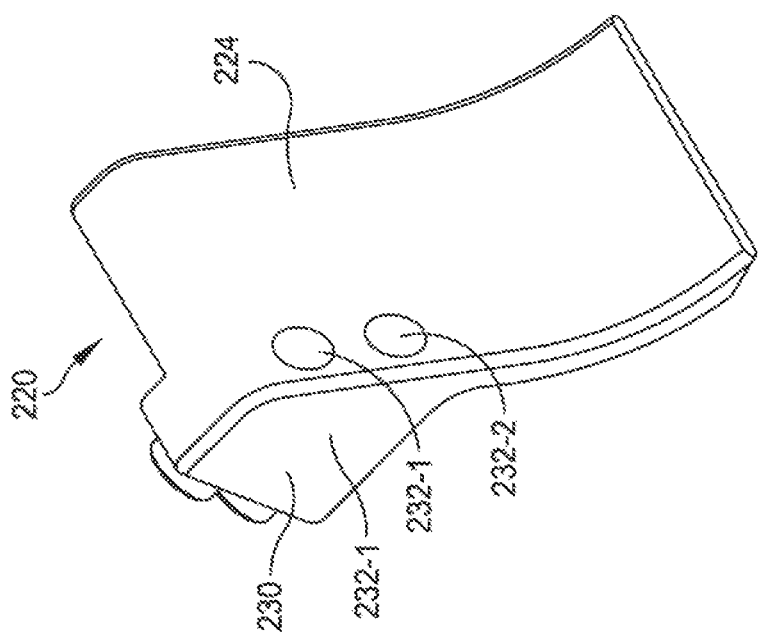
FIG. 13 is an isometric view of another component of the foot clamp illustrated in FIG. 7 in accordance with some embodiments.

One example of a foot clamp or guide 200, which is also configured to receive one or more pins, is shown in FIGS. 7-20. As shown in FIG. 7, foot clamp 200 may include a first component 202 and a second component 220 each of which may be slideably coupled to base plate 102. The slideable coupling of the components 202, 220 of foot clamp 200 advantageously enable feet of a wide variety of sizes to be secured to base plate 102. The foot clamp 200 may incorporate positioning and size variations, which are designed for a single patient or a general range of patient sizes.

As best seen in FIGS. 8-12, component 202 includes a body 204 having a first contoured surface 206 that is curved to approximate the contours of a heel of a human foot. A flange 208 extends from base of the body 204 and includes features (e.g., an extension or dovetail) for engaging one or more of channels 116 defined by base plate 102. In some embodiments, flange 208 defines a slot 210 that extends along a length of flange 208. Slot 210 has a width that is dimensioned to receive a screw or other fixation device for securing component 202 to base plate 102 at a specific location. For example, in some embodiments, base plate 102 may include one or more threaded holes (holes 118-1, 118-2, 118-3, 118-4; collectively "holes 118") for receiving the screw. Rotating the screw to advance the screw into one of the one or more holes hole defined by base plate 102 results in component 202 being pressed against base plate 102 to prevent or resist component 202 moving relative to base plate 102 as will be understood by one of ordinary skill in the art.

Component 202 also includes an extension block 212 extending from an upper surface of the body 204. One or more holes (holes 214-1, 214-2; collectively "holes 214") are defined by extension block 212. Holes 214 extend entirely through extension block 212 and are dimensioned to receive a pin therein. In some embodiments, holes 214 extend parallel to one another, although one of ordinary skill in the art will understand that holes 214 may be otherwise positioned with respect to one another. The one or more pins may be inserted into the one or more holes 214 defined by extension block 212 to secure a foot or extremity to component 202 and thus to base plate 102 when component 202 is secured to base plate 102.

As best seen in FIGS. 13-17, component 220 of foot clamp or guide 200 may have a similar structure to component 202 with the exception that component 220 is essentially a mirror image of component 202. For example, component 220 includes a body 222 having a first contoured surface 224 that is curved to approximate the contours of a heel of a human foot. However, one of ordinary skill in the art will understand that components 202 and 202 may have different shapes such that they would not be considered mirror images of one another.

Figure 15:
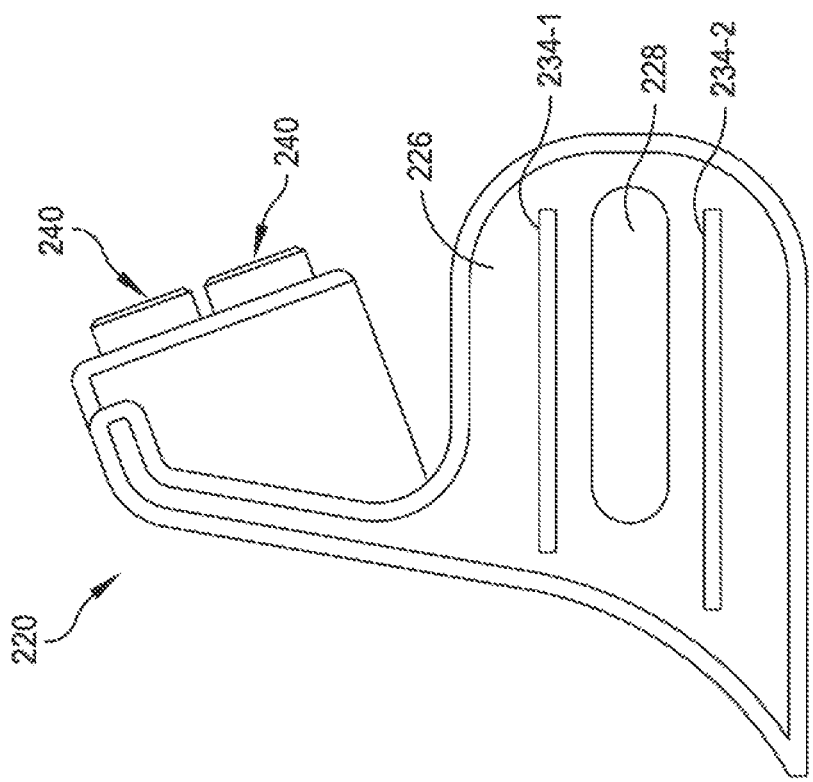
FIG. 15 is a bottom side plan view of the foot clamp component illustrated in FIG. 13 in accordance with some embodiments.
Figure 14:
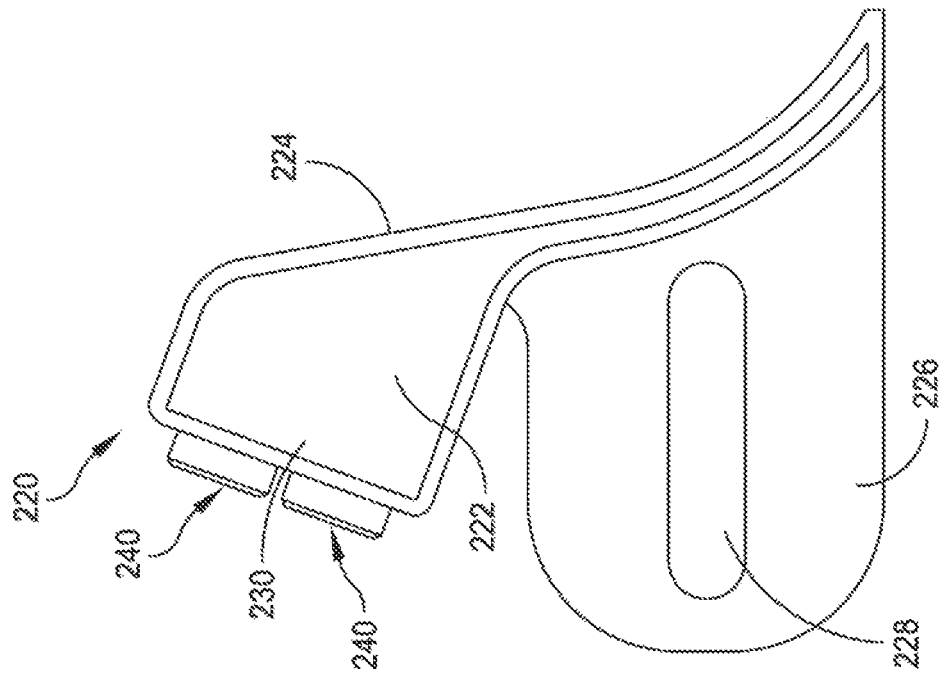
FIG. 14 is a top side plan view of the foot clamp component illustrated in FIG. 13 in accordance with some embodiments.
Figure 17:
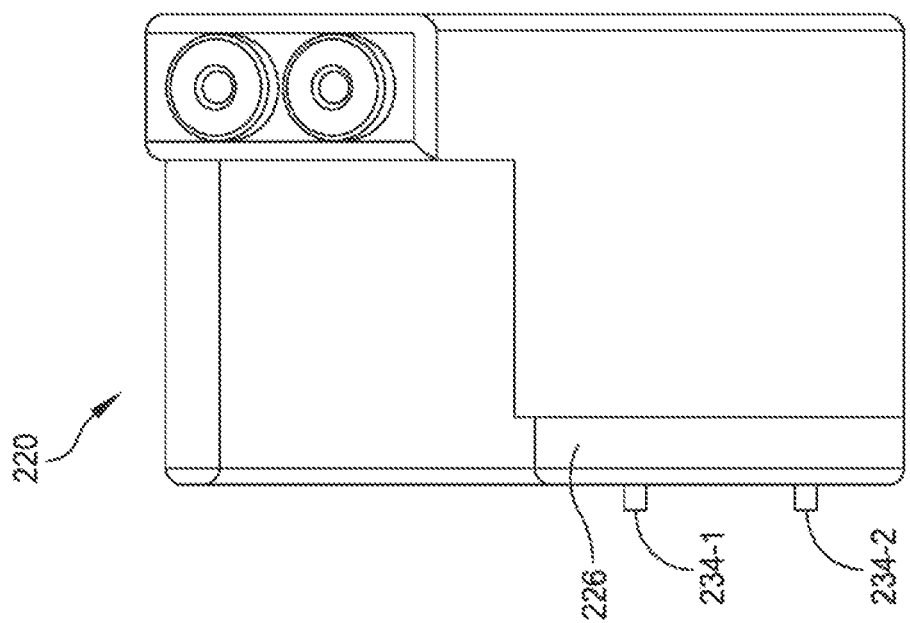
FIG. 17 is a side view of the foot clamp component illustrated in FIG. 13 in accordance with some embodiments.
Figure 16:
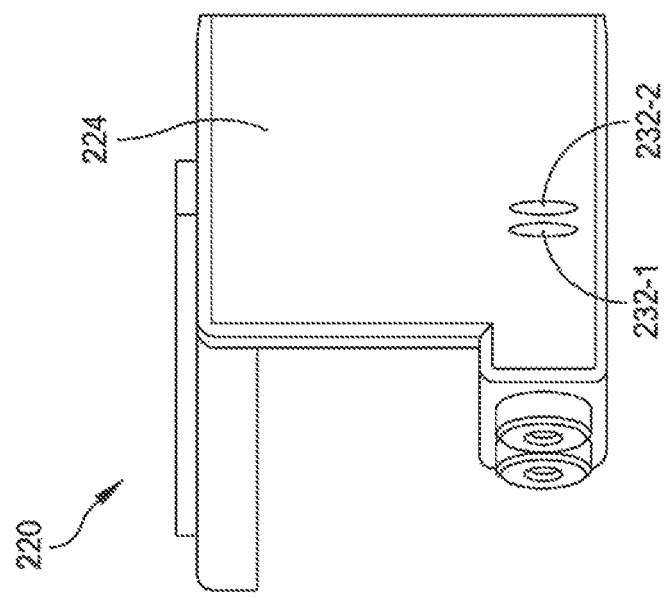
FIG. 16 is an end view of the foot clamp component illustrated in FIG. 13 in accordance with some embodiments.

The body 222 of component 220 may also include a flange 226. Like flange 208 of component 202, the bottom surface of flange 226 may include one or more features (e.g., ribs or a dovetail) 234-1, 234-2 (collectively, "features 234" or "ribs 234") sized and configured to engage one or more of channels 116 defined by base plate 102 as best seen in FIG. 15. In some embodiments, flange 226 defines a slot 228 that extends along a length of flange 226. Slot 228 has a width that is dimensioned to receive a screw or other fixation device for securing component 220 to base plate 102 at a specific location. For example, as described above, base plate 102 may include a number of threaded holes 118 for receiving the screw or fixation device such that, upon rotating the screw to advance the screw into one of the one or more holes defined by base plate 102, component 220 is pressed against base plate 102 to prevent or resist component 220 from moving relative to base plate 102.

Component 220 may also include an extension block 230, which extends from an upper surface of the body 222 of component 220. Extension block 230 defines one or more holes (232-1, 232-2; collectively "holes 232") each of which extends entirely through extension block 230 and being dimensioned to receive a pin therein. In some embodiments, holes 232 extend parallel to one another, although one of ordinary skill in the art will understand that holes 232 may be otherwise aligned with respect to one another. One or more pins may be inserted into one or more holes defined by extension block 230 to secure a foot or other extremity to component 220 and thus to base plate 102 when component 220 is secured to base plate 102.

Figure 20:
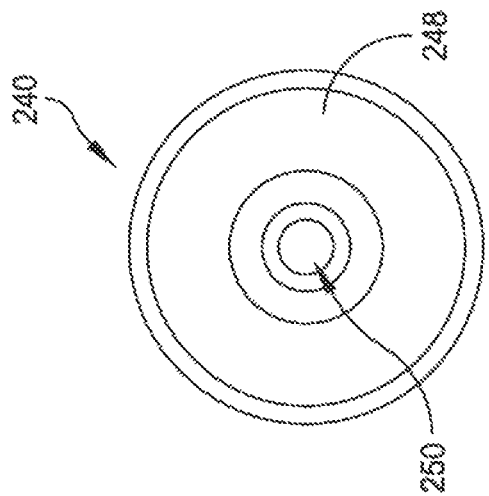
FIG. 20 is a second end view of the insert illustrated in FIG. 18 in accordance with some embodiments.
Figure 18:
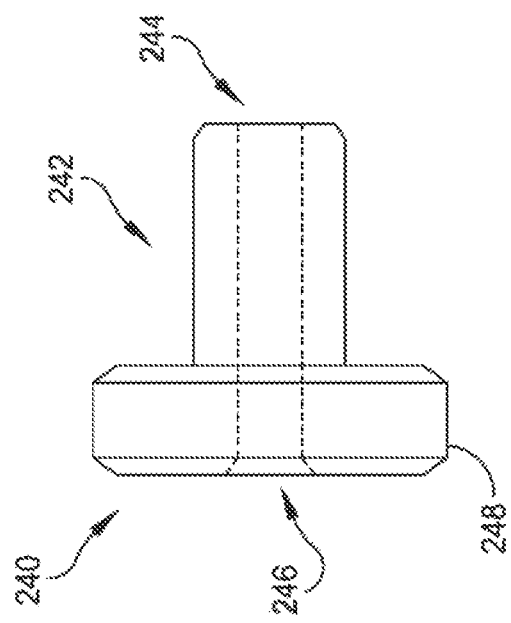
FIG. 18 is a side view of an insert that may be used with the foot clamp illustrated in FIG. 7 in accordance with some embodiments.
Figure 19:
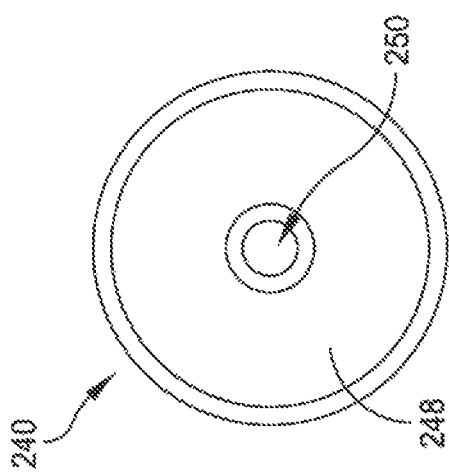
FIG. 19 is a first end view of the insert illustrated in FIG. 18 in accordance with some embodiments.
Figure 21:
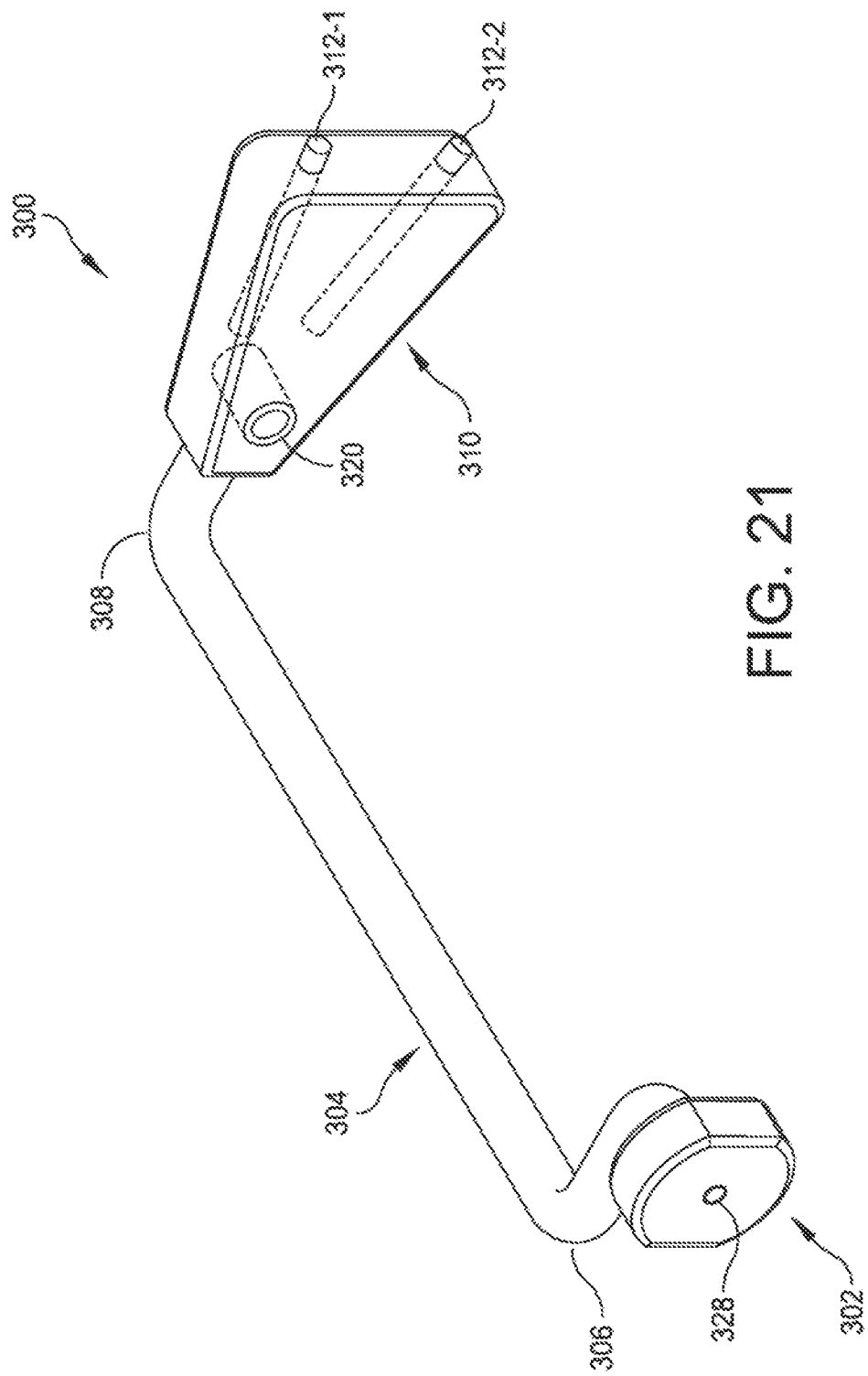
FIG. 21 is an isometric view of a guidance tool in accordance with some embodiments.
Figure 27:
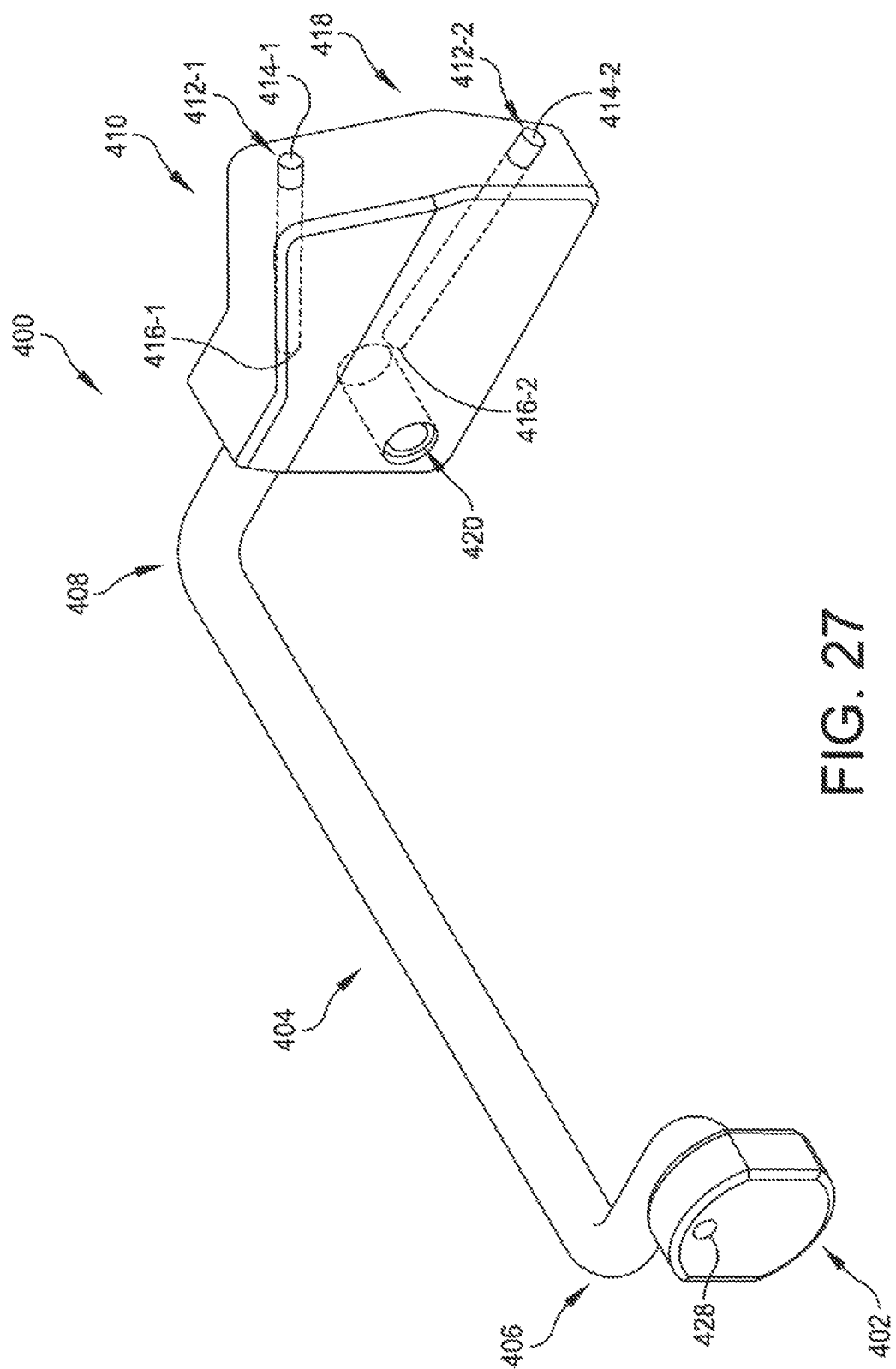
FIG. 27 is an isometric view of another example of a guide tool in accordance with some embodiments.
Figure 33:
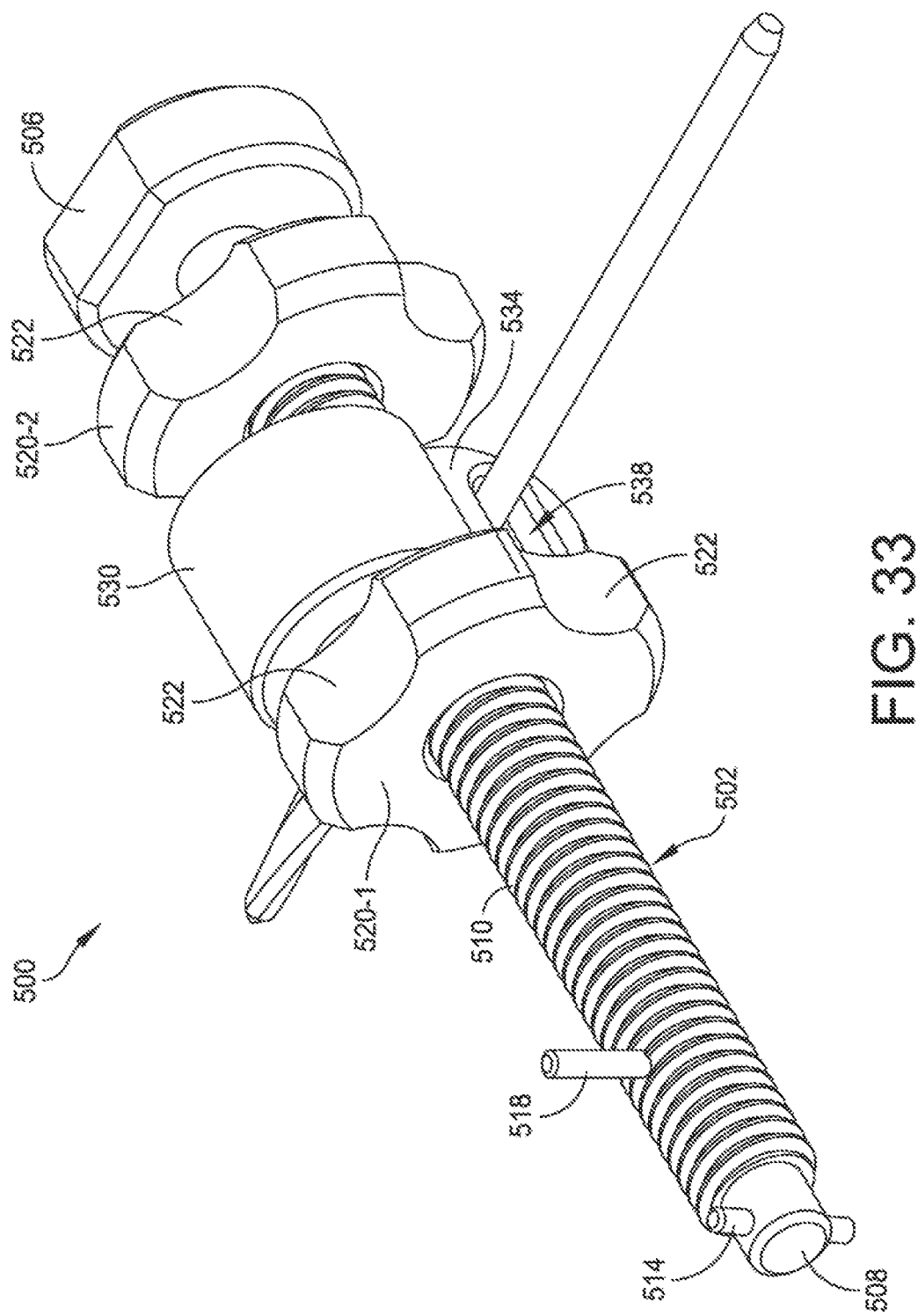
FIG. 33 is an isometric view of a fixation tool in accordance with some embodiments.
Figure 34:
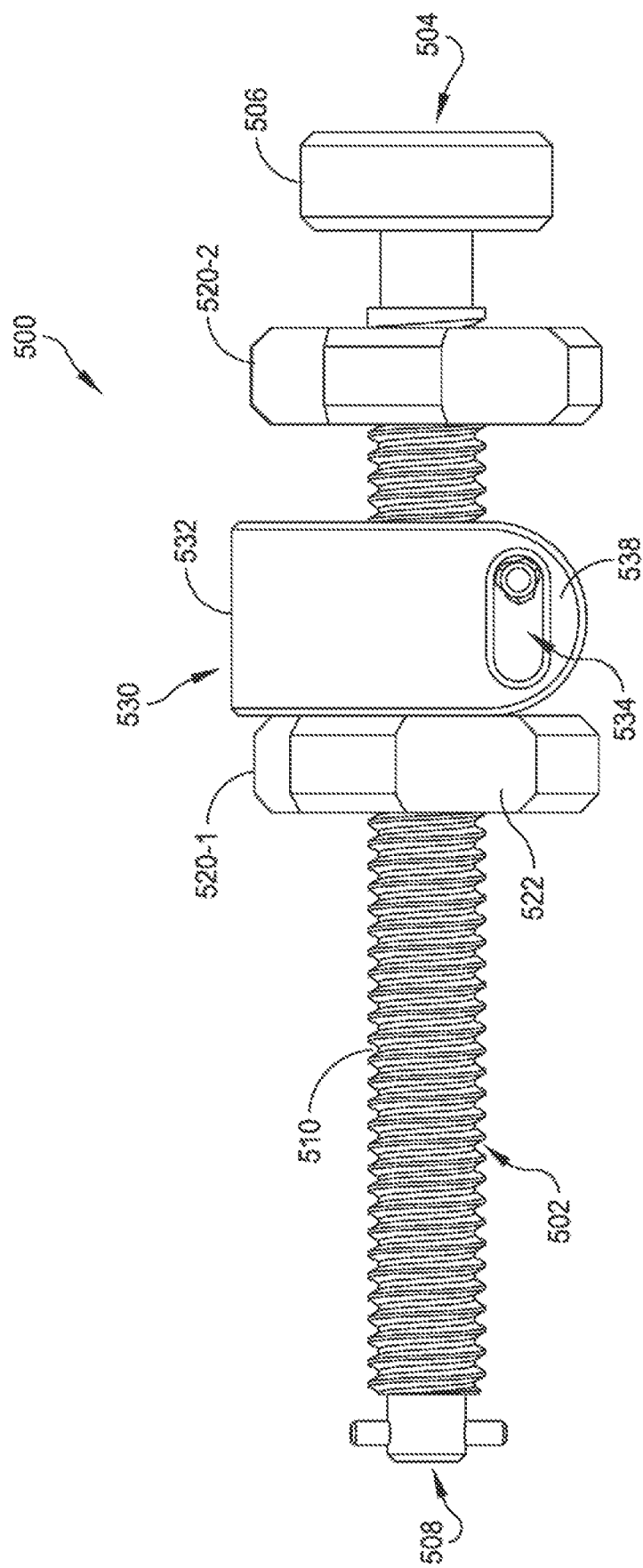
FIG. 34 is a side plan view of the fixation tool illustrated in FIG. 33 in accordance with some embodiments.
Figure 35:
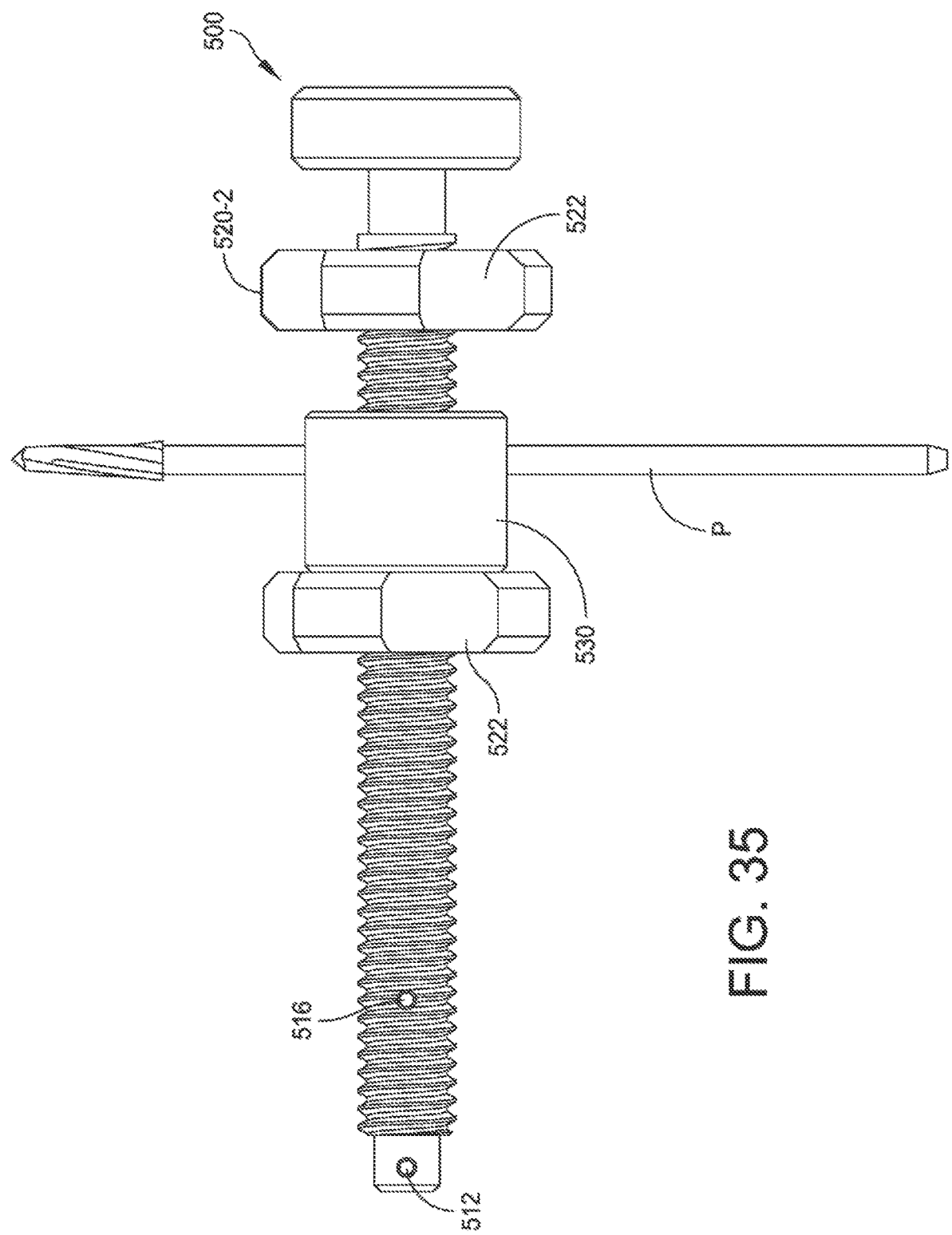
FIG. 35 is another side plan view of the fixation tool illustrated in FIG. 33 in accordance with some embodiments.

To facilitate the use of fluoroscopy, the holes 214, 232 defined by components 202, 220, respectively, may be sized and configured to receive inserts 240 as best seen in FIGS. 18-20. In some embodiments, inserts 240 includes a body 242 longitudinally extending from a first end 244 to a second end 246. Body 242 also may include a shoulder 248 at second end 246. Shoulder 248 has a diameter that is greater than a diameter of the rest body 242, including first end 244. A hole 250 extends through the entirety of body 242 parallel to and, in some embodiments, aligned with a central longitudinal axis defined by body 242. Hole 250 is dimensioned to receive a pin or other fixation device and/or surgical tool (e.g., a drill or burr) as will be understood by one of ordinary skill in the art. Inserts 240 may be press fit (or be dimensioned to have another type of fit) into holes 214, 232 defined by components 202, 220 except that shoulder 248 has a diameter that prevents shoulder 248 from being received within holes 214, 232. The hole 250 may incorporate positioning and size variations which are designed for a single patient or a general range of patient sizes. In some embodiments, inserts 240 are formed from a radiopaque material to provide for fluoroscopic guidance and visualization; however, one of ordinary skill in the art will understand that insert 240 may be formed entirely or partially from a radiopaque material.

FIGS. 21-24 illustrate one example of a first visualization tool 300 that may be used with base plate 102 in accordance with some embodiments. The visualization tool 300 may incorporate positioning and size variations, which are designed for a single patient or a general range of patient sizes.

Visualization tool 300 includes a foot 302 that is sized and configured to engage channels 114 to secure visualization tool 300 to base plate 102. Foot 302 may have a complementary shape to the cross-sectional geometry of channels 114. For example, if channels 114 include a dovetail shape or undercut, then foot 302 may have a complementary dovetail shape or include extensions for being received within the undercut. Although not shown, foot 302 may include a spring loaded detent, a hole for receiving a screw, or other locking mechanism for securing visualization tool 300 to a specific location along the length of channel 114. Foot may also include a radiopaque member 328 for providing a visualization/alignment check in combination with radiopaque member 320 as discussed below.

Visualization tool 300 also includes a stem 304 extending from foot 302 and terminating at body 310. For reasons described in greater detail below, foot 302, stem 304, and body 310 may be formed from a radiolucent material. In some embodiments, stem 304 includes one or more bends 306, 308 or curves for providing a bowed shape to visualization tool 300. Providing visualization tool 300 with a bowed shape increases the amount of area (e.g., clearance) between the extremity fixed to base plate 102 and the stem 304 of visualization tool 300 while at the same time enabling body 310 to be at least partially disposed over the extremity or body part when the extremity or body part is secured to base plate 102.

As best seen in FIG. 24, body 310 may include one or more radiopaque members 312-1, 312-2 (collectively "radiopaque members 312) embedded within and/or otherwise attached to or supported by body 310. In some embodiments, radiopaque members 312 comprise elongate rods and each of which extend from a first end 314 to a second end 316. Radiopaque members are shown as being supported by body 310 such that their longitudinal axes are arranged non-perpendicular and non-parallel with respect to one another, although one of ordinary skill in the art will understand that the rods may aligned such that they are perpendicular or parallel to one another depending on the surgical procedure in which they will be used. Radiopaque members 312 advantageously provide a surgeon with visual guidance when tool 300 is used with fluoroscopy.

As will be understood by one of ordinary skill in the art, the radiopaque members 312 may define "go"/"no go" areas (e.g., areas in which a surgeon make cuts or should not make cuts) or otherwise provide guidance for making a cut. For example, in the embodiment shown in FIGS. 21-24 and as best seen in FIG. 24, the area 318 located between radiopaque members 312 may be the "go" area and the areas located outside of radiopaque members 312 may be the "no go" area.

In some embodiments, body 310 of tool 300 also supports another radiopaque member 320. As best seen in FIGS. 25-26, radiopaque member 320 has a hollow cylindrical shape extending from a first end 322 to a second end 324 and defining a central opening 326. A central axis defined by the central opening 326 is positioned perpendicular to the longitudinal axes defined by radiopaque members 312 such that radiopaque member 320 may be used to ensure that the fluoroscope is aligned properly with base plate 102. For example, when the fluoroscope is aligned properly with alignment tool 300 (and thus with base plate 102), then the radiopaque member 320 will appear to be a circle when viewed using fluoroscope. If the fluoroscope is misaligned with alignment tool 300 (and thus with base plate 102), then the radiopaque member 320 will appear to be non-circular when viewed using the fluoroscope. Further, when visualization tool includes a radiopaque member 328 in foot 302, the combination of radiopaque members 320, 328 may have the appearance of a bullseye (or other shape or appearance) to indicate the fluoroscope is properly aligned with the tool 300.

Although not shown in FIGS. 21-24, body 310 may also define one or more holes or slots sized and configured to receive a drill, burr, or other surgical tool. For example, body 310 may include any number of holes or slots such that tool 300 may be used as a drill and/or cutting guide in addition to providing visual guidance. The body 310 may incorporate positioning and size variations which are designed for a single patient or a general range of patient sizes.

FIGS. 27-30 illustrate one example of a second visualization tool 400 that may be used with base plate 102 in accordance with some embodiments. Visualization tool 400 may be similar to visualization tool 300. For example, visualization tool 400 may include a foot 402 for securing visualization tool 400 to base plate 102. Like foot 302 of tool 300, foot 402 of visualization tool 400 may have a complementary shape to the shape of channels 114 to facilitate engagement and securement of foot 402 in a channel 114. Tool 402 may include a spring-loaded detent, a hole for receiving a screw, or other locking mechanism for securing visualization tool 400 to a specific location along the length of channel 114. In some embodiments, foot 402 includes a radiopaque member 428 for providing a visualization/alignment check in combination with radiopaque member 420 as described below.

A stem 404 extends from foot 402 to body 410 and includes bends or curves 406, 408 along its length. Foot 402, stem 404, and body 410 may be formed from a radiolucent material such that foot 402, stem 404, and body 410 are essentially transparent under fluoroscopy. The bends or curves 406, 408 provide clearance between the stem 404 and an extremity or body part secured to base plate 102.

Body 410 may include one or more radiopaque members 412-1, 412-2 (collectively, "radiopaque members 412") supported by body 410. Radiopaque members 412 may be implemented as elongate rods each of which extends from a first end 414 to a second end 416; however, a person of ordinary skill in the art will understand that radiopaque members 412 may be implemented in other configurations. Like radiopaque members 312, radiopaque members 412 may be positioned relative to one another such that their longitudinal axes are arranged non-perpendicular and non-parallel, although one of ordinary skill in the art will understand that the radiopaque members 412 may be otherwise positioned relative to one another. Further, radiopaque members may be used to provide a surgeon with visual guidance for making free-hand cuts or may identify "go"/"no go" areas. In the embodiment shown in FIG. 27, for example, the area 418 between radiopaque members 412 may be a "go" area and the area outside of radiopaque members 412 may be a "no go" area.

Body 410 may also support additional radiopaque members beyond radiopaque members 412. For example, body 410 supports radiopaque member 420, which is shown as a hollow cylinder in FIGS. 31 and 32. As best seen in FIG. 32, radiopaque member 420 extends from a first end 422 to a second end 424 and defines a central opening 426 therethrough. A central axis defined by the central opening 426 is positioned perpendicular to the longitudinal axes defined by radiopaque members 412 such that radiopaque member 420 may be used to ensure that the fluoroscope is aligned properly with base plate 102. For example, when the fluoroscope is aligned properly with alignment tool 400 (and thus with base plate 102), then the radiopaque member 420 will appear to be a circle when viewed using fluoroscope. If the fluoroscope is misaligned with alignment tool 400 (and thus with base plate 102), then the radiopaque member 420 will appear to be non-circular when viewed using the fluoroscope. Further, in embodiments in which foot 402 also includes a radiopaque member 428, the combination of radiopaque members 420, 428 may have the appearance of a bullseye (or other shape or appearance) to indicate the fluoroscope is properly aligned with the tool 400. As best seen in FIGS. 29 and 30, in some embodiments the radiopaque member 428 located in the foot 402 is not disposed directly beneath the radiopaque member 420 located in body 410. Consequently, the fluoroscope must be positioned at an angle (e.g., non-parallel) relative to a planar surface of the base plate 102 for the radiopaque members 420, 428 to align properly with one another. A person of ordinary skill in the art will understand that the angle may vary.

Although not shown in FIGS. 27-30, body 410 may also define one or more holes or slots sized and configured to receive a drill, burr, or other surgical tool. For example, body 410 may include any number of holes or slots such that tool 400 may be used as a drill and/or cutting guide in addition to providing visual guidance.

FIGS. 33-36 illustrate one example of a fixation tool 500 that may be used in connection with base plate 102 in accordance with some embodiments. Fixation tool 500 is configured to be secured to base plate 102 and hold one or more pins to secure an extremity or other body part to base plate 102.

Tool 500 includes a base 502 extending from a first end 504, at which a foot 506 is located, to a second end 508. In some embodiments, base 502 includes one or more sections of threads 510 along its length. For example, in some embodiments, base 502 of tool 500 is threaded entirely along its length while in some embodiments base 502 includes one or more discrete sections of threads. Foot 506 is sized and configured to engage channels 114 defined by base plate 102 and to secure tool 500 to a specific location along a length a channel 114. For example, if channels 114 include a dovetail shape or have an undercut, then foot 506 may have a complementary dovetail shape or include extensions for being received within the undercut. Further, the foot 506 of tool 500 may include a spring-loaded detent, a hole for receiving a screw, or other locking mechanism for securing tool 500 to a specific location along the length of channel 114.

In some embodiments, end 508 defines a hole 512 for receiving a dowel pin 514 therethrough. Base 502 may define a second hole 516 disposed along a length therefore for receiving a second dowel pin 518. As described in greater detail below, pins 514, 518 may act as a stop to maintain tool 500 in an assembled configuration.

One or more nuts 520-1, 520-2 (collectively, "nuts 520") may be threadably coupled to the threads 510 of base 502. Nuts 520 may have a generally cylindrical shape with one or more cutouts or recesses 522 to facilitate a user grasping or otherwise engaging nuts 520 in order to rotate nuts 520 about the base 502. As described in greater detail below, rotating nuts 520 relative to base 502 causes nuts 520 to move along a longitudinal axis defined by base 502.

Figure 36:
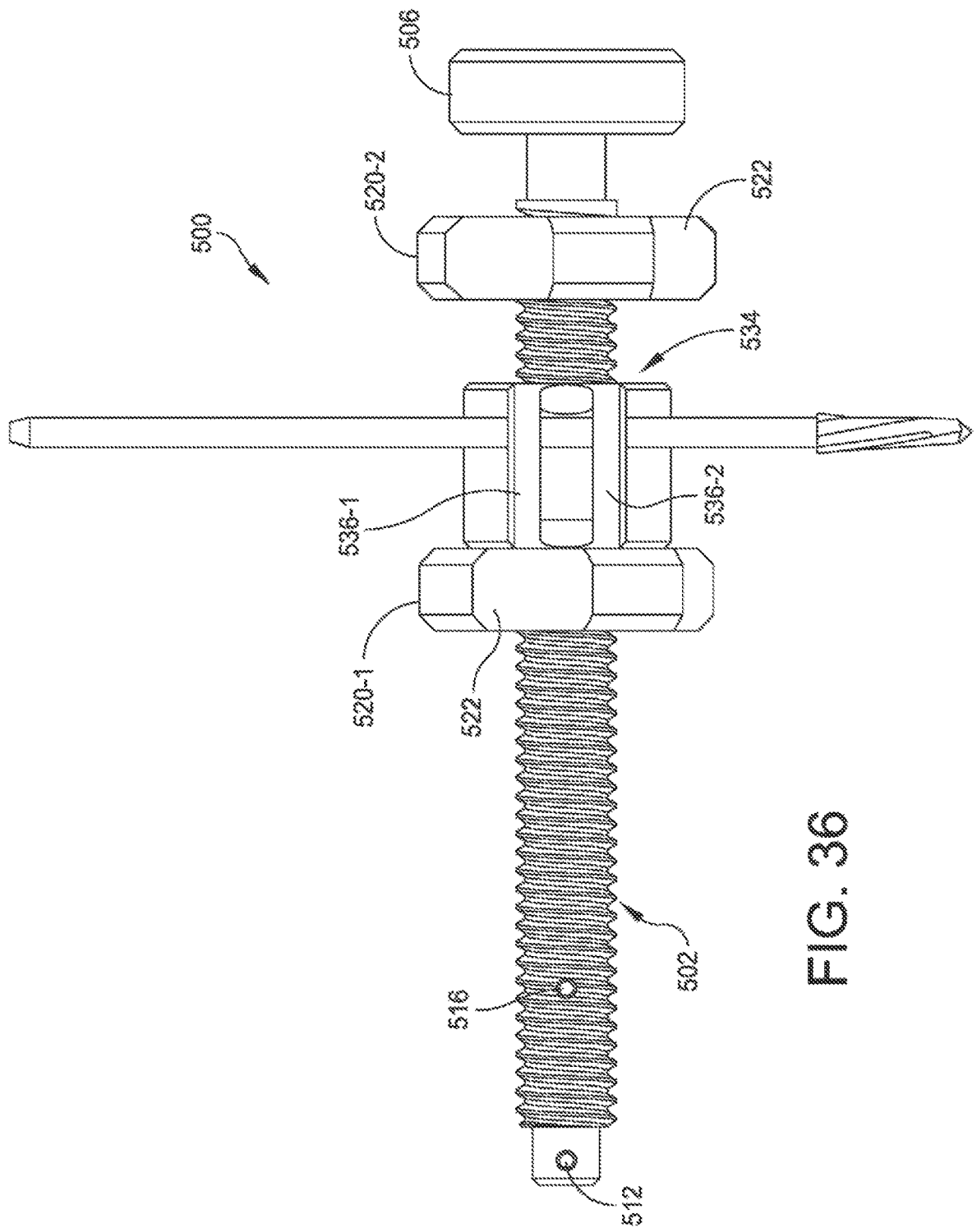
FIG. 36 is another side plan view of the fixation tool illustrated in FIG. 33 in accordance with some embodiments.

A tool guide 530 may also be provided and position between nuts 520 along the length of base 502. In some embodiments, tool guide 530 includes a body 532 having a generally circular outer shape and a flange portion 534 extending therefrom. Flange portion 534 may include a pair of spaced-apart flanges 536-1, 536-2 (collectively, "flanges 536") as best seen in FIG. 36. Each flange 536 may define a respective hole or slot 538 that is dimensioned to receive a fixation or cutting tool, such as a drill or a burr, therethrough in a slideable manner.

As noted above, tool guide 530 may be positioned between nuts 520. Nuts 520 may be used to position tool guide 530 and, consequently, a tool passing through tool guide 530, along the length of base 502 in a position selected by a user. For example, rotating the nuts 520 in a first direction may cause the nuts 520, and thus the tool guide 530, to translate along the length of the base 502 in one direction (e.g., upwardly away from foot 506), and rotating the nuts 520 in a second or opposite direction may cause the nuts 520, and thus the tool guide 530, to translate along the length of the base 502 in an opposite direction (e.g., downwardly toward foot 506). When the desired position of the tool guide 530 has been achieved, then the nuts 520 are rotated in opposite directions relative to one another to "lock" the tool guide 530 in place.

FIGS. 37-42 illustrate one example of a guidance and fixation tool in accordance with some embodiments. In some embodiments, guidance and fixation tool 600 includes a first component 602, e.g., a guidance component, and a second component 612, e.g., a fixation component. Guidance component 602 includes a foot 604 coupled to a stem 606, which in turn is coupled to a body 608. Foot 604 is sized and configured to engage channels 114 defined by base plate 102 and to secure component 602 to a specific location along a length a channel 114. For example, if channels 114 include a dovetail shape or have an undercut, then foot 602 may have a complementary dovetail shape or include extensions for being received within the undercut. Further, the foot 604 of component 602 may include a spring-loaded detent, a hole for receiving a screw, or other locking mechanism for securing component 602 to a specific location along the length of channel 114.

Figure 40:
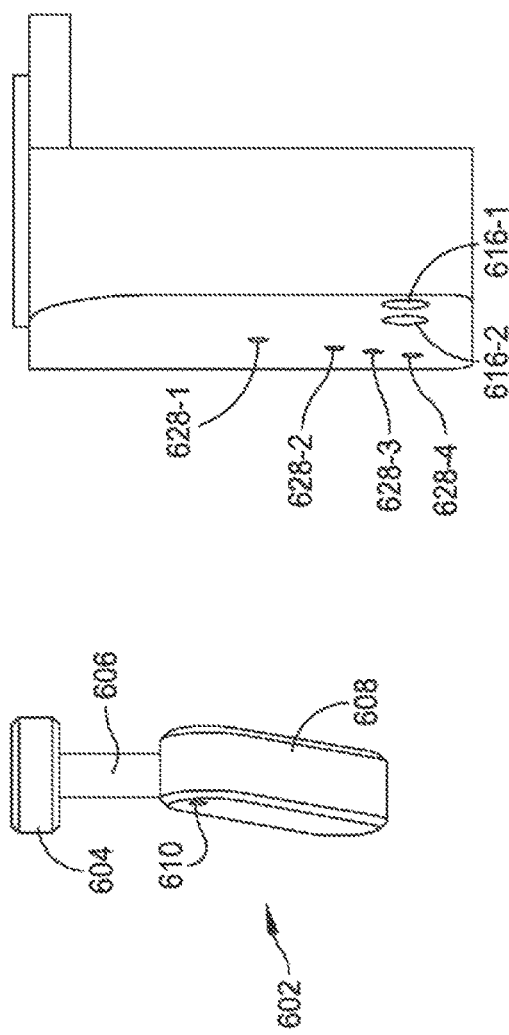
FIG. 40 is a rear view of the guidance and fixation tool illustrated in FIG. 37 n accordance with some embodiments.
Figure 42:
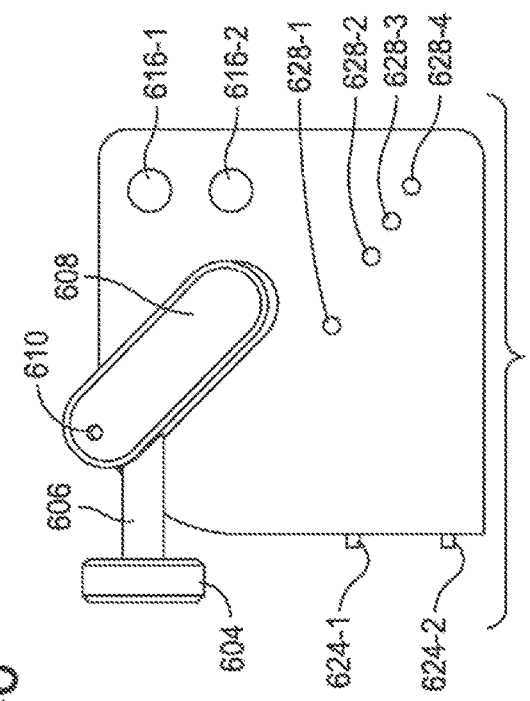
FIG. 42 is another side view of the guidance and fixation tool illustrated in FIG. 37 in accordance with some embodiments.

In some embodiments, body 608 may define a hole 610 as best seen in FIGS. 40 and 42. Body 608 may be formed from a radiolucent material and, although not shown in the figures, one of ordinary skill in the art will understand that body 608 may support one or more radiopaque elements. For example, body 608 may include one or more embedded radiopaque elements that provide for fluoroscopic guidance and/or targeting in combination with radiopaque elements 628 supported by component 612 as described below.

Component 612 includes a body 614 defining one or more holes 616-1, 616-2 (collectively, "holes 616") sized and configured to receive a fixation element therethrough. In some embodiments, holes 616 may be sized and configured to receive a radiopaque insert, such as radiopaque insert 240, described above, and/or a cutting tool or burr. Body 614 may also define a hole 618 sized and configured to receive a radiopaque element, such as a radiopaque member 320 described above.

Figure 37:
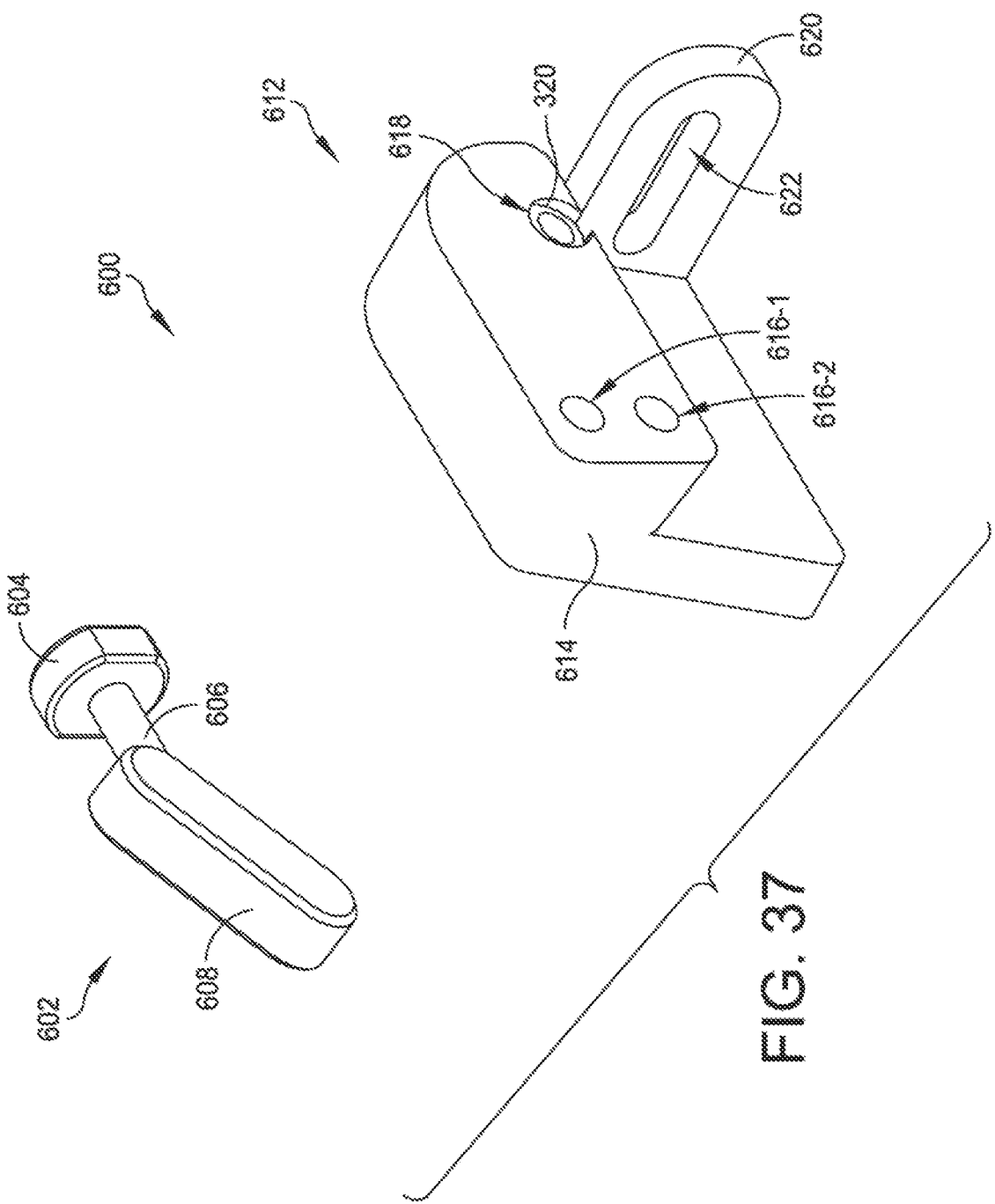
FIG. 37 is an isometric view of one example of a guidance and fixation tool in accordance with some embodiments.
Figure 38:
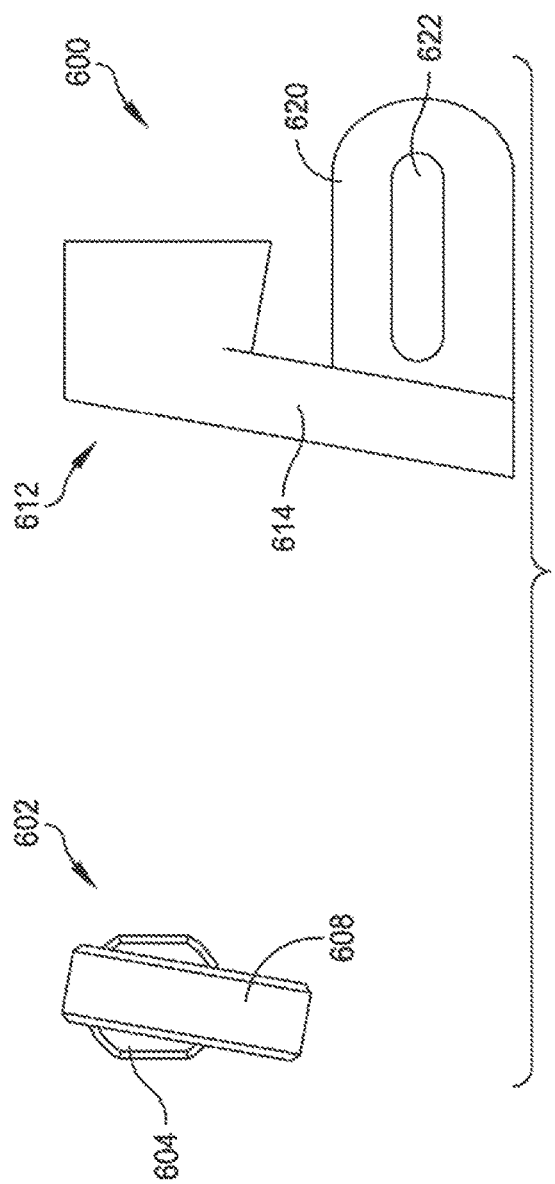
FIG. 38 is a top side plan view of the guidance and fixation tool illustrated in FIG. 37 in accordance with some embodiments.
Figure 39:
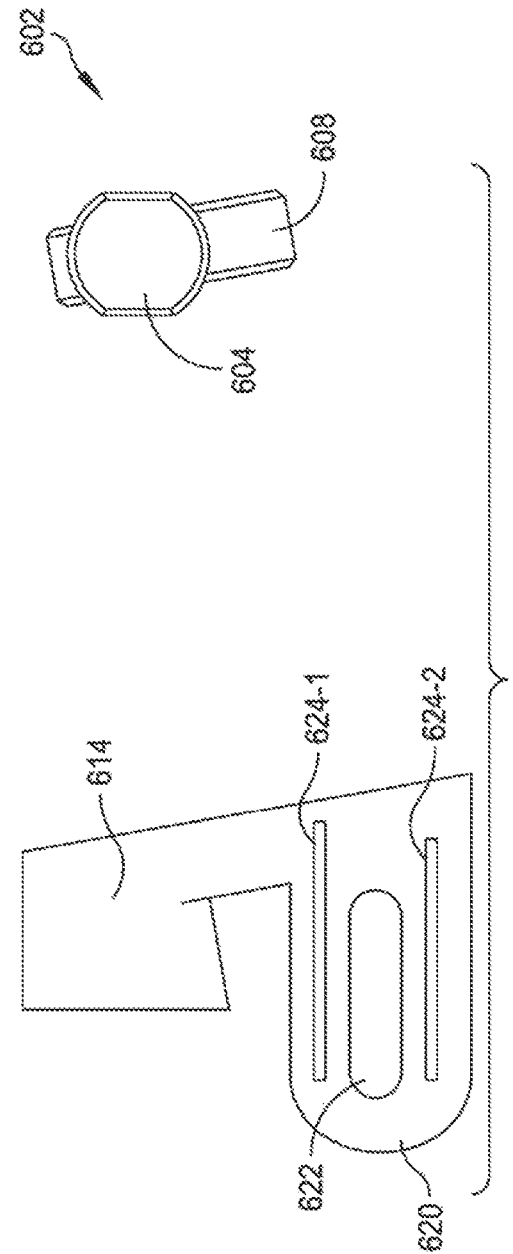
FIG. 39 is a bottom side plan view of the guidance and fixation tool illustrated in FIG. 37 in accordance with some embodiments.
Figure 41:
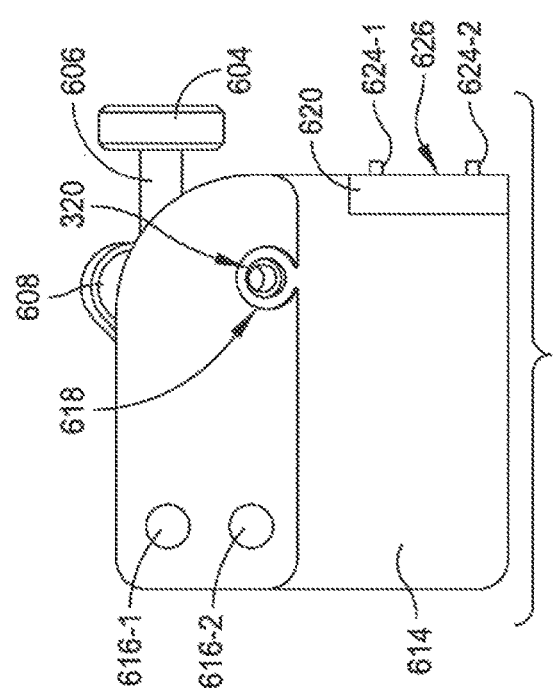
FIG. 41 is a side view of the guidance and fixation tool illustrated in FIG. 37 in accordance with some embodiments.

Component 612 also includes a flange 620 extending from body 614 and defining a slot 622 (FIGS. 37-39). Slot 622 may be sized and configured to receive a fixation device, such as a screw or bolt, for securing slot 622 to base plate 102. As best seen in FIGS. 39 and 41, flange 620 also includes one or more ribs 624-1, 624-2 (collectively, "ribs 624") extending from bottom surface 626 of flange 620. In some embodiments, as shown in FIG. 39, ribs 624 may be disposed on either side of and extend parallel to slot 622. Ribs 624 are sized and configured to be received within channels 116 defined by base plate 102. As best seen in FIG. 42, body 614 may also define a plurality of holes or include a plurality of radiopaque elements serving as targeting guides 628-1, 628-2, 628-3, 628-4 (collectively, "targeting guides 628") that may be seen using fluoroscopy. For example, in some embodiments, the radiopaque element 610 of component 602 may be aligned with the radiopaque elements 628 of component 612 when the components 602, 612 are properly aligned with each other and the fluoroscope is properly aligned with the components 602, 612.

Method of Use

As noted above, the various tools and components may be used as a system in support of various minimally invasive surgical procedures. For example, in some embodiments the various tools and components may be used in performing a MIS procedure associated with a foot as described below. However, one of ordinary skill in the art will understand that the tools and components may be used to perform MIS procedures associated with a hand, wrist, or other extremity.

In some embodiments, a fixture 100 may be formed using the base plate 102 and a foot clamp or guide 200. For example, the components 202, 220 of foot clamp 200 are coupled to the foot plate 102 by aligning the extension or dovetail of the respective component 202, 220 with one of the channels 116 defined by base plate 102. A screw, bolt, or other fixation device may be inserted through the slot 210 defined by component 202 and through slot 228 defined by component 220 and into a hole 118 defined by foot plate 102 to secure the components 202, 220 to base plate 102. As will be understood by one of ordinary skill in the art, the screws, bolts, or other fixation devices may be tightened such that the components 202, 220 of foot clamp 200 may still be moved relative to base plate 102.

A patient's foot may be placed on the base plate 102 and the foot clamp 200 may be adjusted, e.g., by sliding the components 202, 220 of foot clamp 200 relative to base plate 102, until the surgeon or practitioner has achieved the desired positioning. Once the desired positioning has been achieved, the screws, bolts, or other fixation devices may be tightened to secure the foot clamp 200 to base plate 102 and one or more pins may be inserted through the holes 250 defined by the radiopaque inserts 240 of components 202, 220 and into the foot of a patient.

With the foot secured to base plate 102 by way of the pins inserted through the foot clamp 200, any number of MIS procedures may be performed. In some embodiments, such procedures may be performed with fluoroscopic aids. For example, one or more of tools 300 and/or 400 may be coupled to the base plate 102 to provide fluoroscopic guidance. Tool(s) 300 and/or 400 may be coupled to the base plate 102 by inserting a foot, e.g., foot 302 or foot 402, into a channel 114 either through the opening along the side 106 of base plate 102 or via a hole 120.

The tool(s) 300 and/or 400 may be slid along a channel 114 until its desired position is achieved. As will be understood by one of ordinary skill in the art, the position of the tool(s) 300, 400 relative to the foot may be checked using fluoroscopy. For example, a fluoroscope may be used to determine whether the radiopaque members 312 of tool 300 and/or radiopaque members 412 of tool 400 are in the desired position relative to the bones of the foot. The radiopaque member 320 of tool 300 and/or radiopaque member 420 of tool 400 should appear as a circle (and not an oval or other shape) to ensure that the fluoroscope is properly positioned relative to the base plate 102 and tools 300, 400. Further, as discussed above, the radiopaque members 320, 328 or radiopaque members 420, 428 may have the appearance of a bullseye (or other shape or appearance) to indicate the fluoroscope is properly aligned with the tool(s) 300, 400.

The surgeon or other practitioner may further use fluoroscopy during the surgical procedure. For example, as discussed above, tools 300, 400 may be used to guide a surgeon or practitioner in making bony cuts, drilling a hole, or identifying go/no go areas. One of ordinary skill in the art will appreciate that tools 300, 400 may provide a surgeon or practitioner with fluoroscopic aid in a number of other ways.

In some embodiments, a fixture 100 may be formed using the base plate 102 and one or more fixation tools 500. For example, one or more fixation tools 500 may be coupled to the base plate 102 by sliding a foot 506 into a channel 114 via the opening formed along side 106 of base plate 102 or via hole 120.

A foot hand or other body part may be placed in contact with the base plate 102 and then pins or other fixation elements may be inserted through the hole or slot 538 defined by the flange portion 534 of tool guide 530. In some embodiments, prior to inserting the pin or fixation element into the body part, the height of the hole or slot 538 relative to the upper surface 122 of base plate 102 may be adjusted by rotating nuts 520 such that nuts 520 translate along the length (e.g., longitudinal axis) of base 502. The translation of nuts 520 along the length of base 502 causes tool guide 530 to move along the length of the base 502. In some embodiments, once the desired height of hole or slot 538 has been achieved, the nuts 520 may be rotated in opposite direction to fix the position of the tool guide 530 along the length of base 502.

With the foot secured to base plate 102 by way of the pins inserted through one or more fixation tools 500, any number of MIS procedures may be performed. In some embodiments, such procedures may be performed with fluoroscopic aids. For example, as described above, one or more of tools 300 and/or 400 may be coupled to the base plate 102 to provide fluoroscopic guidance. Tool(s) 300 and/or 400 may be coupled to the base plate 102 by inserting a foot, e.g., foot 302 or foot 402, into a channel 114 either through the opening along the side 106 of base plate 102 or via a hole 120.

The tool(s) 300 and/or 400 may be slid along a channel 114 until its desired position is achieved. Providing two areas of access to channels 114, i.e., via hole 120 and the opening of channels 114 at the side 106, advantageously enables one or more tool(s) 300, 400 to be added to the base plate 102 even with one or more fixation tools 500 already being coupled to the base plate 102.

As will be understood by one of ordinary skill in the art, the position of the tool(s) 300, 400 relative to the foot may be checked using fluoroscopy. For example, a fluoroscope may be used to determine whether the radiopaque members 312 of tool 300 and/or radiopaque members 412 of tool 400 are in the desired position relative to the bones of the foot. The radiopaque member 320 of tool 300 and/or radiopaque member 420 of tool 400 should appear as a circle (and not an oval or other shape) to ensure that the fluoroscope is properly positioned relative to the base plate 102 and tools 300, 400.

The surgeon or other practitioner may further use fluoroscopy during the surgical procedure. For example, as discussed above, tools 300, 400 may be used to guide a surgeon or practitioner in making bony cuts, drilling a hole, or identifying go/no go areas. One of ordinary skill in the art will appreciate that tools 300, 400 may provide a surgeon or practitioner with fluoroscopic aid in a number of other ways.

In some embodiments, a fixture 100 may be formed using the foot plate 102, a foot clamp or guide 200, and one or more fixation tools 500. For example, as described above, the components 202, 220 of foot clamp 200 may be coupled to the foot plate 102 by aligning the extension or dovetail of the respective component 202, 220 with one of the channels 116 defined by base plate 102. A screw, bolt, or other fixation device may be inserted through the slot 210 defined by component 202 and through slot 228 defined by component 220 and into a hole 116 defined by foot plate 102 to secure the components 202, 220 to base plate 102. In some embodiments, the screws, bolts, or other fixation devices may be tightened such that the components 202, 220 of foot clamp 200 may still be moved relative to base plate 102.

A patient's foot may be placed on the base plate 102 and the foot clamp 200 may be adjusted, e.g., by sliding the components 202, 220 of foot clamp 200 relative to base plate 102, until the surgeon or practitioner has achieved the desired positioning. Once the desired positioning has been achieved, the screws, bolts, or other fixation devices may be tightened to secure the foot clamp 200 to base plate 102 and one or more pins may be inserted through the holes 250 defined by the radiopaque inserts 240 of components 202, 220 and into the foot of a patient.

Fixation tools 500 may be used to further secure the foot to the base plate 102. As described above, a fixation tool 500 may be placed into engagement with the base plate 102 by sliding foot 504 into a channel 114 either by way of the opening formed along side 106 or via a hole 120. The fixation tool is slid along channel 114 until the desired position is achieved relative to the foot, and then pins or other fixation elements may be inserted through the hole or slot 538 defined by the flange portion 534 of tool guide 530. In some embodiments, prior to inserting the pin or fixation element into the body part, the height of the hole or slot 538 relative to the upper surface 122 of base plate 102 may be adjusted by rotating nuts 520 such that nuts 520 translate along the length (e.g., longitudinal axis) of base 502. The translation of nuts 520 along the length of base 502 causes tool guide 530 to move along the length of the base 502. In some embodiments, once the desired height of hole or slot 538 has been achieved, the nuts 520 may be rotated in opposite direction to fix the position of the tool guide 530 along the length of base 502.

With the foot secured to base plate 102 by way of the pins inserted through foot clamp 200 and one or more fixation tools 500, any number of MIS procedures may be performed. In some embodiments, such procedures may be performed with fluoroscopic aids. For example, as described above, one or more of tools 300 and/or 400 may be coupled to the base plate 102 to provide fluoroscopic guidance. Tool(s) 300 and/or 400 may be coupled to the base plate 102 by inserting a foot, e.g., foot 302 or foot 402, into a slot 114 either through the opening along the side 106 of base plate 102 or via a hole 120.

The tool(s) 300 and/or 400 may be slid along a slot 114 until its desired position is achieved. Providing two areas of access to slots 114, i.e., via hole 120 and the opening of slots 114 at the side 106, advantageously enables one or more tool(s) 300, 400 to be added to the base plate 102 even with one or more fixation tools 500 already being coupled to the base plate 102.

As will be understood by one of ordinary skill in the art, the position of the tool(s) 300, 400 relative to the foot may be checked using fluoroscopy. For example, a fluoroscope may be used to determine whether the radiopaque members 312 of tool 300 and/or radiopaque members 412 of tool 400 are in the desired position relative to the bones of the foot. The radiopaque member 320 of tool 300 and/or radiopaque member 420 of tool 400 should appear as a circle (and not an oval or other shape) to ensure that the fluoroscope is properly positioned relative to the base plate 102 and tools 300, 400.

The surgeon or other practitioner may further use fluoroscopy during the surgical procedure. For example, as discussed above, tools 300, 400 may be used to guide a surgeon or practitioner in making bony cuts, drilling a hole, or identifying go / no go areas. One of ordinary skill in the art will appreciate that tools 300, 400 may provide a surgeon or practitioner with fluoroscopic aid in a number of other ways.

In some embodiments, a fixture 100 may be formed using the base plate 102 guidance and fixation tool 600 and one or more fixation tools 500. For example, component 602 of tool 600 may be coupled to base plate 102 by sliding foot 604 into a channel 114 defined by base plate 102. Component 612 may be coupled to base plate 102 by inserting ribs 624 into channels 116 defined by base plate 102. A screw, bolt, or other fixation device may be inserted into slot 622 defined by the flange 620 of component 612 and into a hole 118 to secure component 612 to base plate 102.

A body part (e.g., hand, foot, wrist) may be secured to the base plate 102 via tool 600 by inserting one or more fixation elements, such as a pin or k-wire, through holes 616 defined by body 614 of component 612. As noted above, an insert 240 may be disposed within holes 616 and a fixation element may be inserted through insert 240 into the body part.

If desired, one or more fixation tools 500 may be used to further secure the body part to the base plate 102. As described above, a fixation tool 500 may be placed into engagement with the base plate 102 by sliding foot 504 into a channel 114 either by way of the opening formed along side 106 or via a hole 120. The fixation tool is slid along channel 114 until the desired position is achieved relative to the foot, and then pins or other fixation elements may be inserted through the hole or slot 538 defined by the flange portion 534 of tool guide 530. In some embodiments, prior to inserting the pin or fixation element into the body part, the height of the hole or slot 538 relative to the upper surface 122 of base plate 102 may be adjusted by rotating nuts 520 such that nuts 520 translate along the length (e.g., longitudinal axis) of base 502. The translation of nuts 520 along the length of base 502 causes tool guide 530 to move along the length of the base 502. In some embodiments, once the desired height of hole or slot 538 has been achieved, the nuts 520 may be rotated in opposite direction to fix the position of the tool guide 530 along the length of base 502.

With the body part secured to base plate 102, any number of MIS procedures may be performed. In some embodiments, such procedures may be performed with fluoroscopic aids, such as one or more of tools 300 and/or 400. As described above, tool(s) 300 and/or 400 may be coupled to the base plate 102 by inserting a foot, e.g., foot 302 or foot 402, into a slot 114 either through the opening along the side 106 of base plate 102 or via a hole 120.

The tool(s) 300 and/or 400 may be slid along a slot 114 until its desired position is achieved. Providing two areas of access to slots 114, i.e., via hole 120 and the opening of slots 114 at the side 106, advantageously enables one or more tool(s) 300, 400 to be added to the base plate 102 even with one or more fixation tools 500 already being coupled to the base plate 102.

As will be understood by one of ordinary skill in the art, the position of the tool(s) 300, 400 relative to the foot may be checked using fluoroscopy. For example, a fluoroscope may be used to determine whether the radiopaque members 312 of tool 300 and/or radiopaque members 412 of tool 400 are in the desired position relative to the bones of the foot. The radiopaque member 320 of tool 300 and/or radiopaque member 420 of tool 400 should appear as a circle (and not an oval or other shape) to ensure that the fluoroscope is properly positioned relative to the base plate 102 and tools 300, 400.

The surgeon or other practitioner may further use fluoroscopy during the surgical procedure. For example, as discussed above, tools 300, 400 may be used to guide a surgeon or practitioner in making bony cuts, drilling a hole, or identifying go/no go areas. One of ordinary skill in the art will appreciate that tools 300, 400 may provide a surgeon or practitioner with fluoroscopic aid in a number of other ways.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system, comprising:
    a first tool comprising a base extending from a first end to a second end and including at least one thread disposed along a length thereof, the first end including a foot having a widthwise dimension that is greater than a diameter of the at least one thread,
    a first nut configured to be disposed along the length of the base and to engage at least one thread,
    a second tool including a foot, a stem coupled to the foot, the stem extending from a first end that is coupled to the foot to a second end, and a body coupled to the second end of the stem formed from a radiolucent material and supporting a first radiopaque member and a second radiopaque member, each of the first and second radiopaque members include an elongate rod, the first and second radiopaque members being supported by the body such that the first and second radiopaque members are spaced apart from one another,
    a base plate having a first side and a second side, the first side of the base plate defining at least one first channel and at least one second channel, the at least one first channel extending along a length of the base plate in a first direction, the at least one second channel extending along a width of the based plate in a second direction, which is different from the first direction, and
    a tool guide configured to be slideably disposed along the length of the base, the tool guide having a body including a flange portion, the flange portion defining an opening sized and configured to receive at least one of a pin and a cutting tool therethrough,
    wherein rotation of the first nut causes the nut to translate along the length of the base thereby causing the tool guide to move along the length of the base.

2. The system of claim 1, wherein the first tool includes a second nut configured to be disposed along the length of the base and to engage the at least one thread.

3. The system of claim 1, wherein the base defines a hole adjacent to the second end of the base, the hole sized and configured to receive a dowel therein.

4. The system of claim 1, wherein the foot of the first tool is sized and configured to be slideably received within the at least one first channel.

5. The system of claim 1, wherein the foot of the second tool is sized and configured to be slideably received within the at least one first channel defined by the base plate.

6. The system of claim 1, wherein the body of the second tool supports a third radiopaque member, the third radiopaque member having a hollow cylindrical configuration and being supported by the body of the second tool such that a central axis defined by the hollow cylinder is perpendicular to a longitudinal axis defined by at least one of the first and second radiopaque members.

* * * * *